US010939884B2

(12) United States Patent
Nariyuki et al.

(10) Patent No.: US 10,939,884 B2
(45) Date of Patent: Mar. 9, 2021

(54) RADIATION EMITTING DEVICE COMPRISING A COMPUTING UNIT FOR CONTROLLING AN INCLINATION AND A ROTATION ANGLE OF A MONITOR, METHOD FOR CONTROLLING RADIATION EMITTING DEVICE, AND PROGRAM

(71) Applicant: FUJIFILM Corporation, Tokyo (JP)

(72) Inventors: Fumito Nariyuki, Kanagawa (JP); Ryosuke Ogura, Kanagawa (JP); Masayoshi Matsuura, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 289 days.

(21) Appl. No.: 15/865,408

(22) Filed: Jan. 9, 2018

(65) Prior Publication Data
US 2018/0146937 A1    May 31, 2018

Related U.S. Application Data

(63) Continuation of application No. PCT/JP2016/003266, filed on Jul. 11, 2016.

(30) Foreign Application Priority Data

Jul. 21, 2015 (JP) .............................. JP2015-143837

(51) Int. Cl.
*A61B 6/00* (2006.01)
*A61B 5/00* (2006.01)
*H04N 5/32* (2006.01)

(52) U.S. Cl.
CPC ............ *A61B 6/462* (2013.01); *A61B 5/0059* (2013.01); *A61B 6/00* (2013.01); *A61B 6/40* (2013.01);
(Continued)

(58) Field of Classification Search
CPC ....... A61B 6/42; A61B 6/4208; A61B 6/4258; A61B 6/4283; A61B 6/44; A61B 6/4405;
(Continued)

(56) References Cited

U.S. PATENT DOCUMENTS 7,250,922 B2 *  7/2007  Sakaniwa ............ A61B 6/4464
                                              345/1.1
7,447,296 B2 * 11/2008  Bruijns .................... A61B 6/00
                                              378/190
(Continued)

FOREIGN PATENT DOCUMENTS

CN      103989486 A     8/2014
JP      H01-119616 U    8/1989
(Continued)

OTHER PUBLICATIONS

Toshiba Medical Supply Co., Ltd., Radiography Apparatus IPF-21, [online], [Searched on Jul. 30, 1999], Internet <URL: http://www.toshiba-iryouyouhin.co.jp/tmeds/xrays/ipf21.html>, 4 pages.
(Continued)

*Primary Examiner* — Allen C. Ho
(74) *Attorney, Agent, or Firm* — Sughrue Mion, PLLC

(57) ABSTRACT

A radiation emitting device includes a radiation source unit that irradiates a subject with radiation, a camera that captures an image of the subject to acquire a captured image of the subject, and a monitor that displays the captured image. A control device controls at least one of the inclination or the rotation angle of the monitor on the basis of at least one of the direction of the radiation source unit, the inclination of a radiation detector, and the rotation angle of the radiation detector, or the display content of the monitor.

18 Claims, 15 Drawing Sheets

(52) U.S. Cl.
CPC .......... *A61B 6/4208* (2013.01); *A61B 6/4258* (2013.01); *A61B 6/44* (2013.01); *A61B 6/4405* (2013.01); *A61B 6/4411* (2013.01); *A61B 6/4429* (2013.01); *A61B 6/4452* (2013.01); *A61B 6/4458* (2013.01); *A61B 6/46* (2013.01); *A61B 6/461* (2013.01); *A61B 6/463* (2013.01); *A61B 6/467* (2013.01); *A61B 6/52* (2013.01); *A61B 6/54* (2013.01); *A61B 6/542* (2013.01); *A61B 6/544* (2013.01); *A61B 6/545* (2013.01); *A61B 6/58* (2013.01); *A61B 6/582* (2013.01); *A61B 6/587* (2013.01); *A61B 6/588* (2013.01); *A61B 6/589* (2013.01); *H04N 5/3205* (2013.01); *A61B 6/4283* (2013.01)

(58) Field of Classification Search
CPC ... A61B 6/4411; A61B 6/4429; A61B 6/4452; A61B 6/4458; A61B 6/46; A61B 6/461; A61B 6/462; A61B 6/463; A61B 6/467; A61B 6/54; A61B 6/542; A61B 6/545; A61B 6/58; A61B 6/587; A61B 6/40; A61B 6/588; A61B 6/589
USPC .............. 378/62, 98, 189, 196–198, 205, 91
See application file for complete search history.

(56) References Cited

U.S. PATENT DOCUMENTS

| | | | | |
|---|---|---|---|---|
| 7,581,884 B1* | 9/2009 | Barnes | ...................... | A61B 6/06 378/164 |
| 7,841,772 B2* | 11/2010 | Nishii | ...................... | A61B 6/08 378/206 |
| 8,052,325 B2* | 11/2011 | Hibino | ...................... | A61B 6/04 378/197 |
| 8,449,183 B2* | 5/2013 | Seimiya | ............... | A61B 6/4464 378/196 |
| 8,651,740 B2* | 2/2014 | Yang | .................... | A61B 6/4476 378/197 |
| 8,849,370 B2* | 9/2014 | Bouvier | ................. | A61B 6/102 600/407 |
| 8,961,011 B2* | 2/2015 | Lalena | ................. | A61B 6/4405 378/197 |
| 9,028,144 B2* | 5/2015 | Choi | ...................... | A61B 6/032 378/205 |
| 9,084,582 B2* | 7/2015 | Omura | ................. | A61B 6/4405 |
| 9,149,247 B2* | 10/2015 | Lee | ....................... | A61B 6/4452 |
| 9,161,727 B2* | 10/2015 | Jenkins | .................... | G21K 1/04 |
| 9,282,940 B2* | 3/2016 | Nishimura | ........... | A61B 6/4405 |
| 9,295,438 B2* | 3/2016 | Omura | ................. | A61B 6/4405 |
| 9,326,747 B2* | 5/2016 | Omura | ................. | A61B 6/4405 |
| 9,413,961 B2* | 8/2016 | Welsh | ................. | A61B 6/4405 |
| 9,642,584 B2* | 5/2017 | Niebler | ............... | A61B 6/4441 |
| 9,649,080 B2* | 5/2017 | Kwak | .................. | A61B 6/4429 |
| 9,662,086 B2* | 5/2017 | Ohta | .................... | A61B 5/0059 |
| 9,693,437 B2* | 6/2017 | Simmons | ............... | G01N 23/04 |
| 9,693,746 B2* | 7/2017 | Ancar | ...................... | A61B 6/08 |
| 9,730,653 B2* | 8/2017 | Niizeki | ................ | A61B 6/4405 |
| 9,782,143 B2* | 10/2017 | Graumann | ............... | A61B 6/54 |
| 9,788,810 B2* | 10/2017 | Ancar | ................... | A61B 6/587 |
| 9,833,209 B2* | 12/2017 | Belei | .................... | A61B 6/4441 |
| 9,949,699 B2* | 4/2018 | Visser | ................... | G06T 11/003 |
| 9,962,138 B2* | 5/2018 | Schweizer | ........... | A61B 6/4476 |
| 9,974,505 B2* | 5/2018 | Lee | ......................... | A61B 6/463 |
| 9,993,221 B2* | 6/2018 | Kim | ....................... | A61B 6/547 |
| 10,064,588 B2* | 9/2018 | Uchida | ................ | A61B 6/4405 |
| 10,098,609 B2* | 10/2018 | Kim | ........................ | A61B 6/587 |
| 10,111,630 B2* | 10/2018 | Du | ........................ | A61B 6/4482 |
| 10,213,170 B2* | 2/2019 | Malm | ...................... | A61B 6/03 |
| 10,258,307 B2* | 4/2019 | Park | ........................ | A61B 6/547 |
| 10,278,654 B2* | 5/2019 | Sadakane | ............... | A61B 6/025 |
| 10,292,673 B2* | 5/2019 | Niizeki | ................ | A61B 6/547 |
| 10,321,880 B2* | 6/2019 | Lerch | ................... | A61B 6/0407 |
| 10,321,884 B2* | 6/2019 | Hayashi | ................ | A61B 6/462 |
| 10,441,242 B2* | 10/2019 | Kim | ........................ | A61B 6/587 |
| 10,456,100 B2* | 10/2019 | Ninomiya | ............ | A61B 6/4452 |
| 10,506,995 B2* | 12/2019 | Ninomiya | ............... | A61B 6/547 |
| 10,709,406 B2* | 7/2020 | Aoshima | ............... | A61B 6/4064 |
| 10,813,617 B2* | 10/2020 | Inoue | ....................... | H05G 1/00 |
| 2011/0049370 A1 | 3/2011 | Yoshida et al. | | |
| 2014/0093045 A1 | 4/2014 | Shimada et al. | | |
| 2014/0233703 A1 | 8/2014 | Omura et al. | | |
| 2015/0350545 A1 | 12/2015 | Welsh | | |
| 2016/0038110 A1 | 2/2016 | Hayashi et al. | | |

FOREIGN PATENT DOCUMENTS

| | | |
|---|---|---|
| JP | H06-142088 A | 5/1994 |
| JP | 2000217808 A | 8/2000 |
| JP | 2007-029353 A | 2/2007 |
| JP | 2009-064014 A | 3/2009 |
| JP | 2009-131323 A | 6/2009 |
| JP | 2010-119485 A | 6/2010 |
| JP | 2012-029889 A | 2/2012 |
| JP | 2012-029916 A | 2/2012 |
| JP | 2013017569 A | 1/2013 |
| JP | 2013123629 A | 6/2013 |
| JP | 2014-068891 A | 4/2014 |
| JP | 2014-155620 A | 8/2014 |
| JP | 2014-210049 A | 11/2014 |
| WO | 2004064639 A1 | 8/2004 |
| WO | 2014027312 A1 | 2/2014 |
| WO | 2014173741 A1 | 10/2014 |
| WO | 2015079119 A1 | 6/2015 |

OTHER PUBLICATIONS

International Search Report of PCT/JP2016/003266 dated Nov. 1, 2016.
Written Opinion of the International Searching Authority dated Nov. 1, 2016, in counterpart International Application No. PCT/JP2016/003266.
International Preliminary Report on Patentability dated Jan. 23, 2018, in counterpart International Application No. PCT/JP2016/003266.
Notification of Reason for Refusal dated Jan. 8, 2019 from the Japanese Patent Office in application No. 2017-529443.
Communication dated May 23, 2018, from European Patent Office in counterpart application No. 16827417.3.
First Office Action dated Jun. 15, 2020 from the China National Intellectual Property Administration in Application No. 201680041856.0.

* cited by examiner

RADIATION EMITTING DEVICE COMPRISING A COMPUTING UNIT FOR CONTROLLING AN INCLINATION AND A ROTATION ANGLE OF A MONITOR, METHOD FOR CONTROLLING RADIATION EMITTING DEVICE, AND PROGRAM

CROSS REFERENCE TO RELATED APPLICATIONS

The present application is a Continuation of PCT International Application No. PCT/JP2016/003266 filed on Jul. 11, 2016, which claims priority under 35 U.S.C. § 119(a) to Japanese Patent Application No. 2015-143837 filed on Jul. 21, 2015. Each of the above applications is hereby expressly incorporated by reference, in its entirety, into the present application.

BACKGROUND

Technical Field

The present invention relates to a radiation emitting device that irradiates a subject with radiation in a case in which a radiographic image of the subject is captured, a method for controlling the radiation emitting device, and a program.

Background Art

For example, as disclosed in JP2012-29889A and Toshiba Medical Supply Co., Ltd., Radiography Apparatus IPF-21, [online], [Searched on Jul. 30, 1999], Internet <URL: http://www.toshiba-iryouyouhin.co.jp/tmeds/xrays/ipf21.html>, a portable radiation emitting device has been proposed which is provided with only a minimum number of components for emitting radiation, such as a radiation source and an electric circuit, and can be operated by an operator while being held in the hand. This type of portable radiation emitting device is light enough to be operated by the operator while being held in the hand and is advantageous in capturing an image of an object in various directions.

In a case in which a radiographic image of a subject is captured by the radiation emitting device, a radiation detector (a so-called "flat panel detector") that records a radiographic image indicating the subject using radiation that has been emitted and transmitted through the subject is generally used. As the radiation detector, a cassette-type radiation detector has been known in which, for example, an image detection unit, a battery for driving, and a control unit, such as an electric circuit related to driving, are accommodated in a housing. The radiation detector is located so as to face the radiation emitting device, with a subject interposed therebetween. In this state, the radiation emitting device is driven. Then, radiation transmitted through the subject is emitted to the radiation detector and a radiographic image indicated by the radiation transmitted through the subject is acquired.

The above-mentioned portable radiation emitting device can be operated by the operator while being held in the hand. However, a radiation emitting device including a support device that supports a radiation source unit including a radiation source has been proposed in order to prevent hand shaking and the exposure of, for example, the hand of the operator to radiation. Toshiba Medical Supply Co., Ltd., Radiography Apparatus IPF-21, [online], [Searched on Jul. 30, 1999], Internet <URL: http://www.toshiba-iryouyouhin-.co.jp/tmeds/xrays/ipf21.html> discloses an example of the support device and particularly discloses a support device which includes a wheel portion provided in a lower part of a support leg and is movable.

A radiation emitting device including the support device basically includes a leg portion that is movable by a wheel, a main body portion that includes a battery for driving a radiation source and an electric circuit related to the driving of the radiation source and is held on the leg portion, and an arm portion that is connected to the main body portion. The radiation source unit is attached to a leading end of the arm portion.

In a case in which the radiation emitting device is used, first, the radiation emitting device is moved close to the bed on which a patient lies. Then, the radiation source unit is moved to a desired position and the radiation detector is moved to a desired position behind the back of the subject. In this state, the radiation source unit is driven to emit radiation to the subject and the radiation detector detects radiation transmitted through the subject and acquires a radiographic image of the subject.

In addition, a method has been proposed which captures an image of a subject with a camera to acquire a captured image indicating the surface of the subject and displays the captured image in order to, for example, recognize a radiation field in a radiography apparatus in which a radiation emitting device and a radiation detector are separately provided (see JP2009-131323A, JP2007-029353A, and JP2010-119485A).

In addition, the movable radiation emitting device is provided with a monitor such as a liquid crystal display that displays a captured radiographic image and various kinds of information required for the setting of the device. In the radiation emitting device including the monitor in which the monitor can be rotated on the center of a display surface, a method has been proposed which changes the arrangement of the display content of the monitor according to the rotation angle of the monitor, that is, whether the monitor is horizontally long or vertically long, which makes it possible to easily check the display content according to the rotation angle of the monitor (see JP2014-155620A).

Furthermore, a radiation emitting device has been known which includes a monitor and a radiation source unit attached to an arm portion that can be expanded and contracted by a nesting structure. In the radiation emitting device in which the arm portion can be expanded and contracted, a method has been proposed which changes the inclination of the monitor, that is, the angle of the monitor with respect to the horizontal plane according to the position of the radiation source unit in a case in which the arm portion is contracted (see JP2014-068891A). In addition, in JP2014-068891A, the inclination of the monitor is changed according to the position of the radiation source unit.

In addition, a method has been proposed which provides a monitor in a main body such that the monitor can be rotated about a vertical axis and face in a desired direction (see JP1989-119616U (JP-H01-119616U)).

Furthermore, a device has been proposed in which a monitor and a radiation source unit are integrated (see JP2012-029916A). In this device, the inclination of the monitor is changed according to the direction of the radiation source unit. Therefore, it is possible to match the direction of the radiation source unit with the direction of a radiographic image displayed on the monitor. As a result, it is possible to easily see the radiographic image.

SUMMARY OF THE INVENTION

The radiation emitting device having the above-mentioned configuration has the advantage that it can be easily moved in a narrow space or it can be used even in an environment in which an alternating current source is not available. Therefore, in particular, for example, the radiation emitting device is appropriately used to capture a radiographic image of the patient who is raced to a medical institution, such as a hospital, or the patient who lies on the bed in a narrow hospital room. As disclosed in JP2014-155620A to JP1989-119616U (JP-H01-119616U), the inclination and rotation angle of the monitor are changed to improve the operability of the device.

However, the method disclosed in JP2014-068891A changes the inclination of the monitor in a case in which the radiation source unit is accommodated and does not change the inclination of the monitor in a case in which the device is operated. In addition, the method disclosed in JP2014-155620A makes it easy to check the display content of the monitor according to the inclination of the monitor. In the method disclosed in JP1989-119616U (JP-H01-119616U), the monitor can be simply rotated about the vertical axis. Therefore, the methods disclosed in JP2014-155620A and JP1989-119616U (JP-H01-119616U) do not change, for example, the rotation angle of the monitor according to a usage state.

A radiation emitting device according to an aspect of the invention comprises: radiation emitting unit for irradiating a subject with radiation; imaging unit for capturing an image of the subject to acquire a captured image of the subject; display unit for displaying the captured image; and control unit for controlling at least one of an inclination or a rotation angle of the display unit, on the basis of at least one of a direction of the radiation emitting unit, an inclination of a radiation detector that detects the radiation transmitted through the subject and generates a radiographic image of the subject, or a rotation angle of the radiation detector, or display content of the display unit.

The "captured image of the subject" is an image indicating the surface of the subject and the surface of objects in the vicinity of the subject in an imaging range of the imaging unit. The captured image of the subject includes an infrared image which is acquired by capturing an image of the subject using infrared rays and indicates the temperature distribution of the surface of the subject and the surface of the objects in the vicinity of the subject.

It is assumed that the term "on the basis of the display content of the display unit" includes a case based on the content of information which includes the captured image and the radiographic image and is displayed on the display unit and a case based on the content of the captured image displayed on the display unit.

The "direction of the radiation emitting unit" means a direction in which radiation is emitted in the radiation emitting unit.

The "inclination of the radiation detector" means the angle of the detection surface of the radiation detector with respect to a reference plane. Here, in a case in which the radiation detector is kept horizontal, the detection surface is horizontal. Therefore, for example, the horizontal plane parallel to the detection surface of the radiation detector in a state in which the radiation detector is kept horizontal can be used as the reference plane. In addition, a plane perpendicular to the horizontal plane may be used as the reference plane.

The "rotation angle of the radiation detector" means an angle determined by rotation about an axis perpendicular to the detection surface of the radiation detector. Specifically, for example, the "rotation angle of the radiation detector" means an angle at which a rectangular radiation detector is disposed so as to be vertically long and is used and an angle at which the rectangular radiation detector is disposed so as to be horizontally long and is used.

The "inclination of the display unit" means the angle of a display surface of the display unit with respect to the reference plane. Here, in a case in which the display unit is kept horizontal, the display surface is horizontal. Therefore, for example, the horizontal plane parallel to the display surface of the display unit in a state in which the display unit is kept horizontal can be used as the reference plane. In addition, a plane perpendicular to the horizontal plane may be used as the reference plane.

The "rotation angle of the display unit" means an angle determined by rotation about an axis perpendicular to the display surface of the display unit. Specifically, for example, the "rotation angle of the display unit" means an angle at which rectangular display unit is used as vertically long display unit and an angle at which the rectangular radiation detector is used as horizontally long display unit.

In the radiation emitting device according to an aspect of the invention, the display unit may have a rectangular shape in which a length of two sides opposite to each other in one direction is different from a length of two sides opposite to each other in the other direction. The radiation emitting device may further comprise driving unit for changing at least one of an inclination or a rotation angle of the display unit. The control unit may control the driving unit such that at least one of the inclination or the rotation angle of the display unit is changed, on the basis of at least one of the direction of the radiation emitting unit, the inclination of the radiation detector that detects the radiation transmitted through the subject and generates the radiographic image of the subject, or the rotation angle of the radiation detector, or the display content of the display unit.

In the radiation emitting device according to an aspect of the invention, in a case in which the radiation detector is included in the captured image displayed on the display unit, the control unit may control at least one of the inclination or the rotation angle of the display unit.

In the radiation emitting device according to an aspect of the invention, in a case in which at least one of the direction or the inclination of the radiation detector is displayed on the display unit, the control unit may control at least one of the inclination or the rotation angle of the display unit.

The "direction of the radiation detector" means a specific direction of the radiation detector on the detection surface. For example, in terms of the structure of the radiation detector, a direction from a lower portion to an upper portion of the detection surface, that is, the vertical direction of the radiation detector can be used as the direction of the radiation detector. In addition, other directions, such as a direction perpendicular to the vertical direction, may be used as the direction of the radiation detector.

In the radiation emitting device according to an aspect of the invention, in a case in which the subject is included in the captured image displayed on the display unit, the control unit may control at least one of the inclination or the rotation angle of the display unit.

In the radiation emitting device according to an aspect of the invention, the control unit may control at least one of the inclination or the rotation angle of the display unit on the basis of a body position of the subject included in the captured image displayed on the display unit.

In the radiation emitting device according to an aspect of the invention, the control unit may match the inclination of the display unit with the inclination of the radiation detector.

In the radiation emitting device according to an aspect of the invention, the control unit may match the rotation angle of the display unit with the rotation angle of the radiation detector.

The term "matching" includes a case in which two items are completely matched with each other and a case in which two items are not completely matched with each other, but are matched to some extent that they are regarded as completely matched with each other.

In the radiation emitting device according to an aspect of the invention, the control unit may control at least one of the inclination or the rotation angle of the display unit on the basis of the display of another image different from the captured image on the display unit.

The term "another image" may be any image different from the captured image. For example, a radiographic image can be used as another image.

In the radiation emitting device according to an aspect of the invention, the control unit may further control brightness of the display unit on the basis of brightness of the captured image.

In the radiation emitting device according to an aspect of the invention, the captured image may be an infrared image and the display unit may display the infrared image and the radiographic image of the subject.

In the radiation emitting device according to an aspect of the invention, the radiation emitting unit may comprise change unit for changing the direction of the radiation emitting unit. The change unit may change the direction of the radiation emitting unit on the basis of the inclination of the radiation detector.

In the radiation emitting device according to an aspect of the invention, the display unit may be provided separately from the radiation emitting unit and the imaging unit. In this case, the control unit may be provided separately from the display unit.

The radiation emitting device according to an aspect of the invention may further comprise: a leg portion that is movable on a device mounting surface with wheels; a main body portion that is held on the leg portion; and an arm portion that is connected to the main body portion. The radiation emitting unit and the imaging unit may be attached to the arm portion. The display unit may be attached to the main body portion. The control unit may be accommodated in the main body portion.

According to an aspect of the invention, there is provided a method for controlling a radiation emitting device comprising radiation emitting unit for irradiating a subject with radiation, imaging unit for capturing an image of the subject to acquire a captured image of the subject, and display unit for displaying the captured image. The method comprises controlling at least one of an inclination or a rotation angle of the display unit, on the basis of at least one of a direction of the radiation emitting unit, an inclination of a radiation detector that detects the radiation transmitted through the subject and generates a radiographic image of the subject, or a rotation angle of the radiation detector, or display content of the display unit.

In addition, a program that causes a computer to perform the method for controlling a radiation emitting device according to an aspect of the invention may be provided.

According to an aspect of the radiation emitting device and the method for controlling the radiation emitting device of the invention, at least one of the inclination or the rotation angle of the display unit is changed on the basis of at least one of the direction of the radiation emitting unit, the inclination of the radiation detector that detects the radiation transmitted through the subject and generates the radiographic image of the subject, or the rotation angle of the radiation detector, or the display content of the display unit. Therefore, it is possible to change at least one of the inclination or the rotation angle of the display unit according to the usage state of the device. As a result, it is possible to improve the usability of the device.

DESCRIPTION OF EMBODIMENTS

Figure 1:
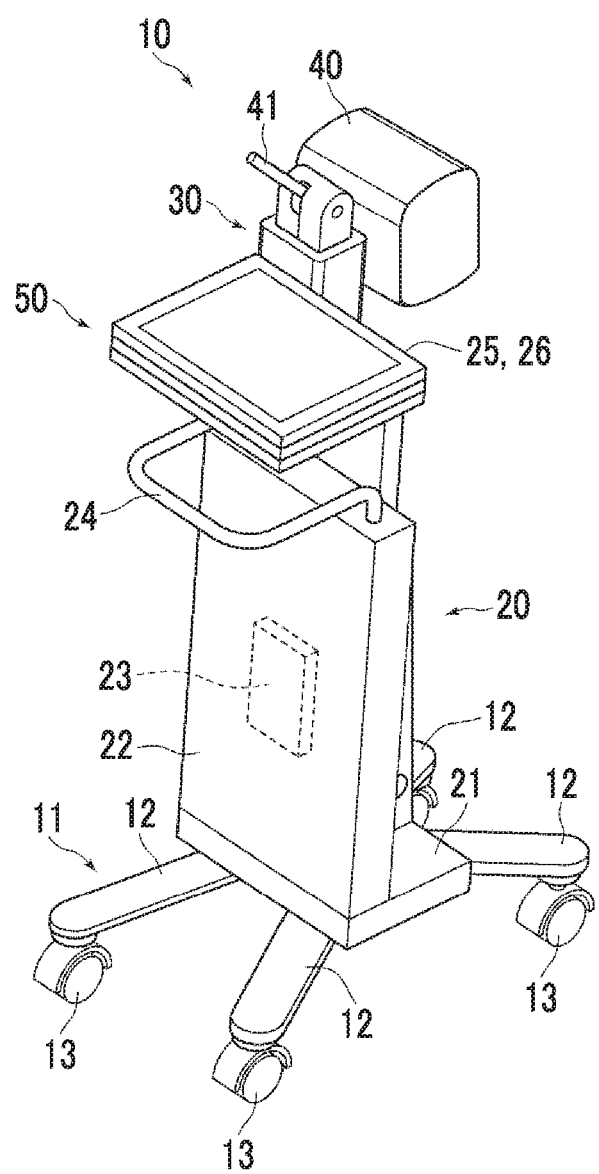
FIG. 1 is a perspective view illustrating the overall shape of a radiation emitting device according to an exemplary embodiment of the invention.
Figure 2:
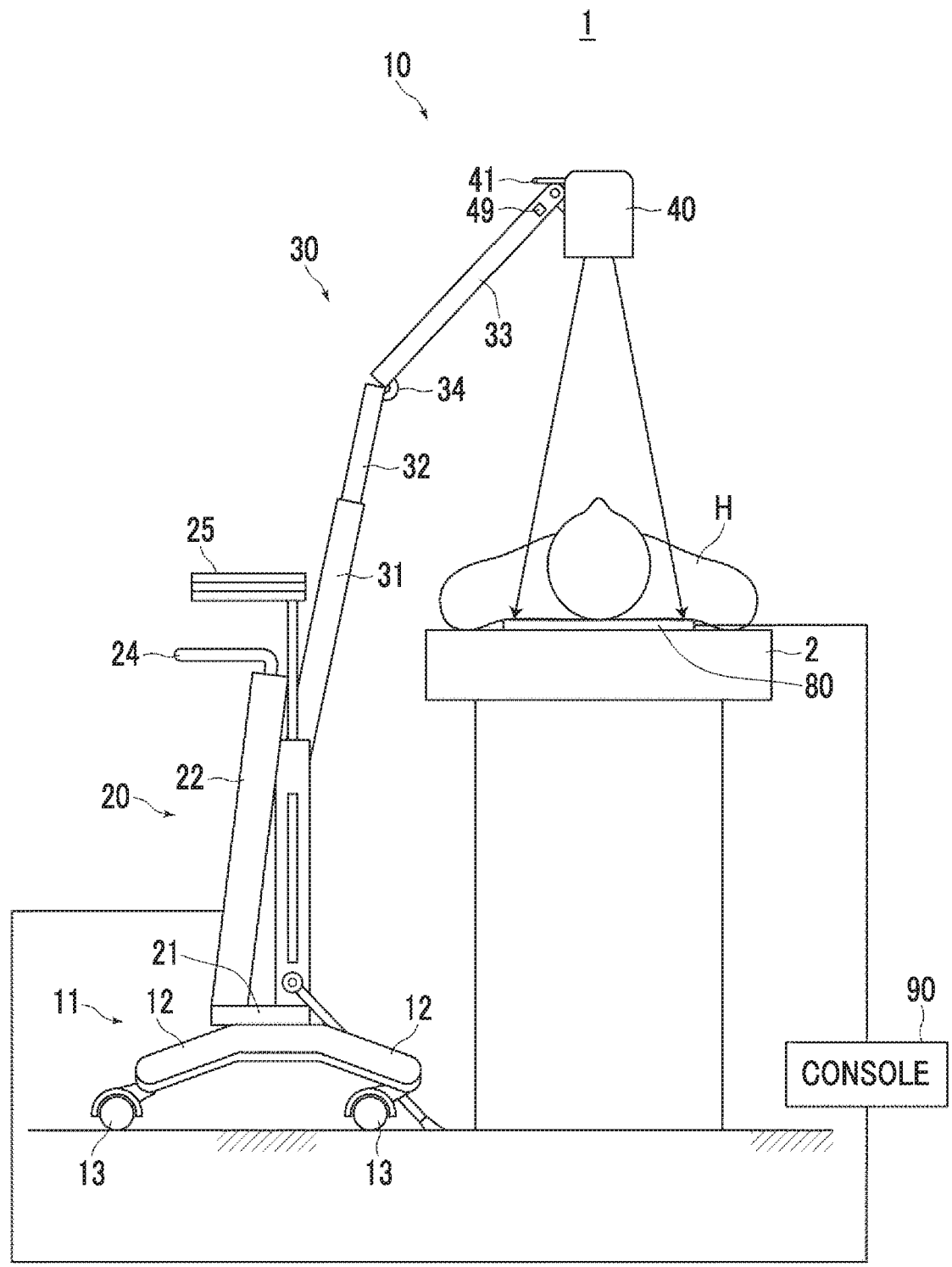
FIG. 2 is a diagram illustrating the usage state of a radiography apparatus including the radiation emitting device according to the exemplary embodiment of the invention.

Hereinafter, exemplary embodiments of the invention will be described with reference to the drawings. FIG. 1 is a perspective view illustrating the overall shape of a radiation emitting device according to an exemplary embodiment of the invention. FIG. 2 is a diagram illustrating the usage state of a radiography apparatus including the radiation emitting device according to the exemplary embodiment of the invention. As illustrated in the drawings, a radiography apparatus 1 according to this exemplary embodiment includes a radiation emitting device 10, a radiation detector 80, and a console 90. For example, in order to acquire a radiographic image of a subject H that lies on a bed 2, the radiation detector 80 is inserted between the subject H and the bed 2, the subject H is irradiated with radiation emitted from the radiation emitting device 10, and a radiographic image of the subject H is acquired by the radiation detector 80.

The radiation emitting device 10 according to this exemplary embodiment is a movable radiation emitting device and includes a leg portion 11 that can be moved on a device mounting surface, a main body portion 20 that is held on the leg portion 11, an arm portion 30 that is connected to the main body portion 20, a radiation source unit 40 that is attached to a leading end of the arm portion 30, and a driving unit 50 that drives a monitor which will be described below.

The leg portion 11 includes four legs 12 and wheel portions 13 that are attached to the lower surfaces of the leading ends of the legs 12. The wheel portion 13 is provided with brake means (not illustrated).

In the main body portion 20, a control device 23 that controls the driving of the radiation emitting device 10 is accommodated in a housing 22 fixed to an upper part of a base portion 21. A handle 24 for moving the radiation emitting device 10 is attached to an upper end of the housing 22. In addition, a monitor 25 and a driving unit 50 for the monitor 25 are attached to the upper part of the base portion 21.

The monitor 25 is, for example, a liquid crystal panel and displays a captured image acquired by a process which will be described below, a radiographic image of the subject H, and various kinds of information required to control the radiation emitting device 10. In addition, the monitor 25 includes a touch-panel-type input unit 26 and receives various commands required to operate the device 10. The monitor 25 corresponds to display unit.

The arm portion 30 includes a plurality of members 31, 32, and 33 having a nesting structure. The member 32 and the member 33 are connected to each other by a rotation holding mechanism 34. The member 33 is rotated with respect to the member 32 in a direction in which the angle is changed.

The radiation source unit 40 is pivotably attached to the leading end of the member 33 of the arm portion 30. A lock lever 41 can be operated to fix the pivot position of the pivotable radiation source unit 40. An angle sensor 49, such as a rotary encoder that detects the pivot angle of the radiation source unit 40, is provided at the leading end of the member 33 of the arm portion 30. Here, it is assumed that the pivot angle of the radiation source unit 40 is 0 degrees in a state in which the radiation source unit 40 directly faces the ground. In addition, the pivot angle indicates the direction of the radiation source unit 40, that is, the emission direction of radiation from the radiation source unit 40. The radiation source unit 40 corresponds to radiation emitting unit.

Figure 3:
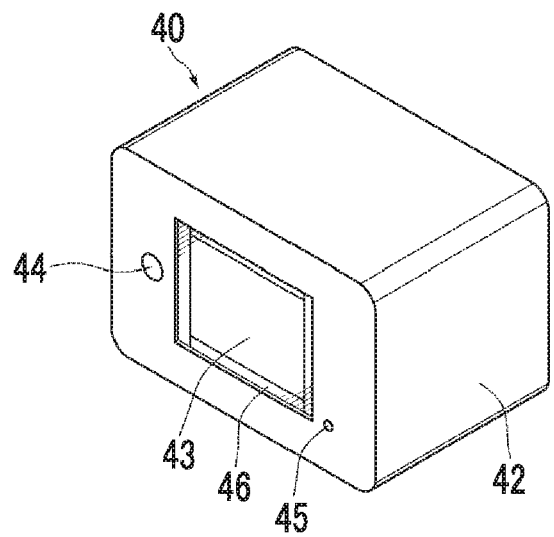
FIG. 3 is a perspective view illustrating the configuration of a radiation source unit as viewed from a radiation emitting side.

FIG. 3 is a perspective view illustrating the configuration of the radiation source unit 40 as viewed from a radiation emitting side. As illustrated in FIG. 3, in the radiation source unit 40, an emission window 43 through which radiation is emitted, a camera 44 that captures an image of the surface of the subject H to acquire a captured image, and a distance sensor 45 are provided on a front surface of a housing 42. A collimator 46 for narrowing the emission range of radiation is seen from the emission window 43. The captured image acquired by the camera 44 is displayed on the monitor 25. The distance sensor 45 measures the distance between the front surface of the radiation source unit 40 and an object, using a laser or ultrasonic waves. The camera 44 corresponds to imaging unit.

Figure 4:
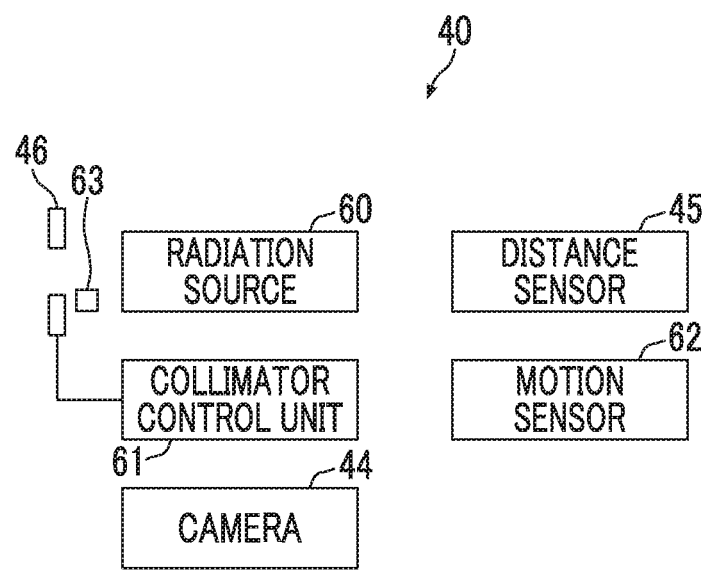
FIG. 4 is a block diagram schematically illustrating the internal configuration of the radiation source unit.

FIG. 4 is a block diagram schematically illustrating the internal configuration of the radiation source unit 40. As illustrated in FIG. 4, the camera 44, the distance sensor 45, a radiation source 60, a collimator control unit 61, a motion sensor 62, and a radiation field lamp 63 are accommodated in the housing 42 of the radiation source unit 40.

The radiation source 60 includes, for example, an X-ray tube, a booster circuit, and cooling means for cooling the X-ray tube.

The collimator control unit 61 includes, for example, a driving mechanism, such as a motor for driving the collimator 46 to change the field of the radiation emitted from the radiation source 60 to the subject H, and an electric circuit for controlling the driving mechanism. The collimator control unit 61 controls the driving of the collimator 46 in response to a command from the control device 23.

The motion sensor 62 is a 9-axis motion sensor that detects 3-axis acceleration, 3-axis angular velocity, and 3-axis tilt. The acceleration, angular velocity, and tilt detected by the motion sensor 62 are output as movement information to the control device 23 and are used to control the radiation emitting device 10 during imaging.

The radiation field lamp 63 is a light emitting element such as a light bulb or a light emitting diode (LED) that emits visible light. The control device 23 controls the turn-on and turn-off of the radiation field lamp 63. When the radiation field lamp 63 is turned on, visible light is emitted to the radiation field in which radiation is emitted on the subject H.

Figure 5:
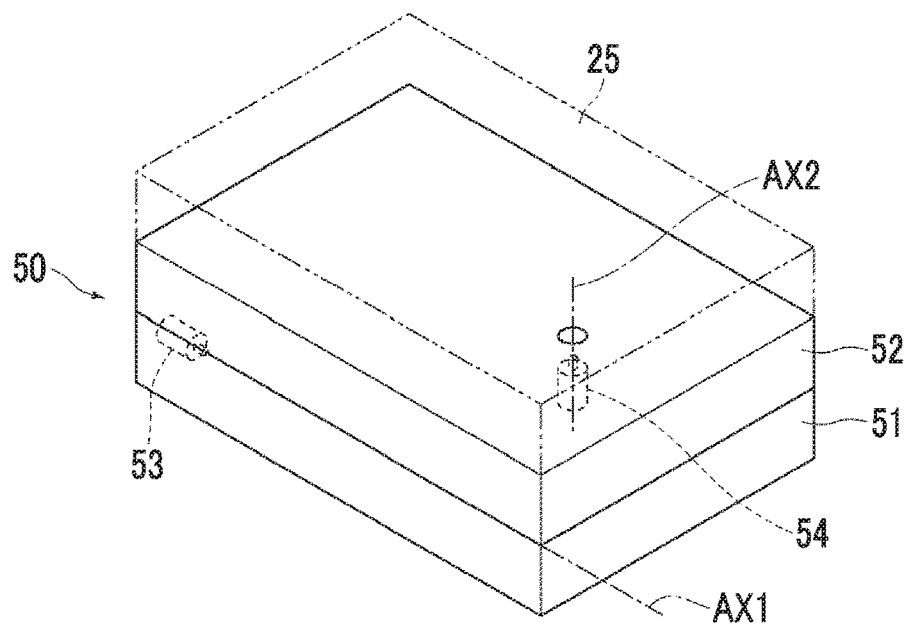
FIG. 5 is a perspective view illustrating the configuration of a driving unit.

FIG. 5 is a perspective view illustrating the configuration of the driving unit 50. As illustrated in FIG. 5, the driving unit 50 includes a housing 51 and a support plate 52 that supports the monitor 25. In FIG. 5, the monitor 25 is represented by a virtual line. A motor 53 that rotates the support plate 52 about an axis AX1 with respect to the housing 51 is accommodated in the housing 51. A motor 54 that rotates the monitor 25 about an axis AX2 is accommodated in the support plate 52.

Figure 6:
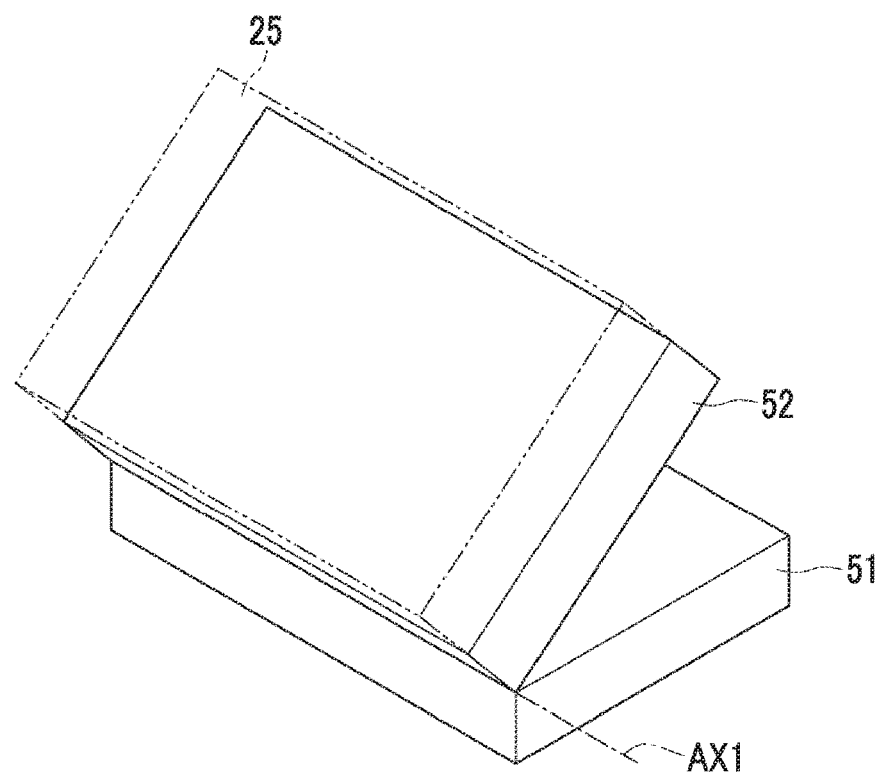
FIG. 6 is a diagram illustrating the usage state of the driving unit.
Figure 7:
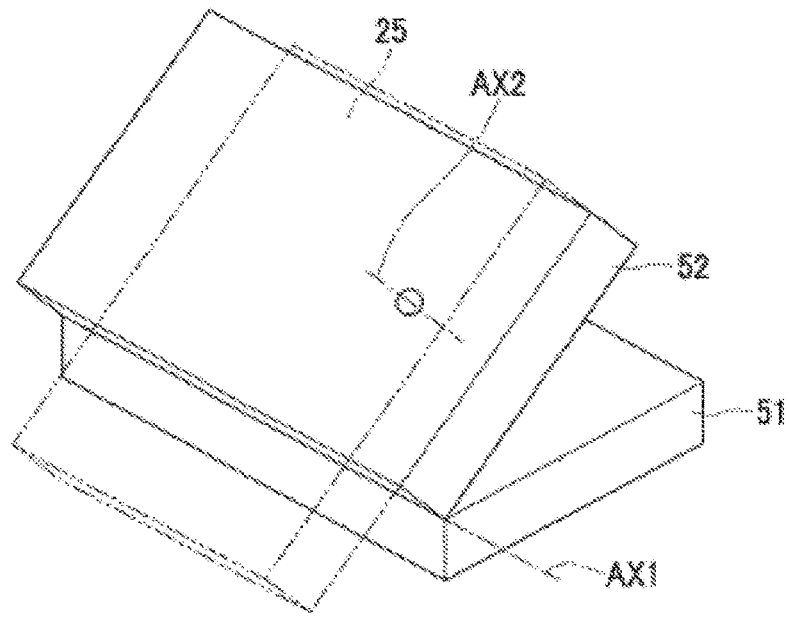
FIG. 7 is a diagram illustrating the usage state of the driving unit.

The motors 53 and 54 are driven by commands from the control device 23. The motor 53 is driven to rotate the support plate 52 about the axis AX1 such that the inclination of the monitor 25 is changed as illustrated in FIG. 6. In the state illustrated in FIG. 6, the motor 54 is driven to rotate the support plate 52 about the axis AX2 such that the monitor 25 is changed from a rotation angle at which the monitor 25 is horizontally long to a rotation angle at which the monitor 25 is vertically long, as illustrated in FIG. 7, or is changed from a rotation angle at which the monitor 25 is vertically long to a rotation angle at which the monitor 25 is horizontally long. In this exemplary embodiment, it is assumed that a state in which the inclination of the monitor 25 is 0, that is, a display surface of the monitor 25 is horizontal and the monitor 25 is at the rotation angle at which the monitor 25 is horizontally long is an initial position. In this case, a reference plane for the inclination of the monitor 25 is the horizontal plane.

Figure 8:
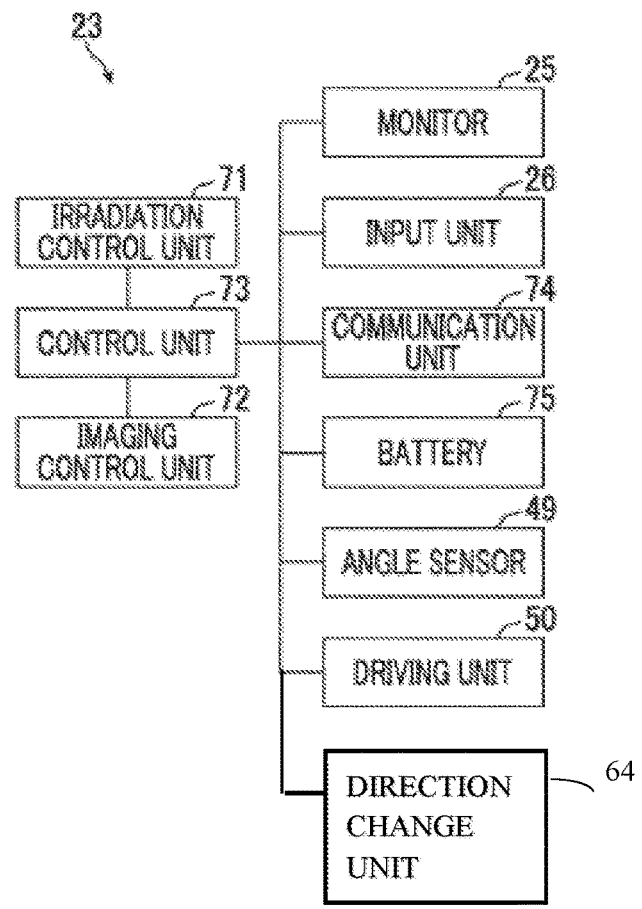
FIG. 8 is a block diagram schematically illustrating the configuration of a control device.

FIG. 8 is a block diagram schematically illustrating the configuration of the control device 23. As illustrated in FIG. 8, the control device 23 includes an irradiation control unit 71, an imaging control unit 72, a control unit 73, a communication unit 74, and a battery 75. Here, for convenience of explanation, FIG. 8 also illustrates the monitor 25, the input unit 26, the angle sensor 49, and the driving unit 50. The irradiation control unit 71, the imaging control unit 72, the control unit 73, and the communication unit 74 are implemented by a program (software) that is operated in a computer, dedicated hardware, or a combination thereof. The program is recorded on a recording medium, such as a digital versatile disc (DVD) or a compact disk read only memory (CD-ROM), and is then distributed. The program is installed in the control device 23 from the recording medium. Alternatively, the program is stored in a storage device of a server computer that is connected to a network or a network storage such that it can be accessed from the outside. The program is downloaded and installed in the control device 23, if necessary.

The irradiation control unit 71 drives the radiation source 60 and controls the amount of radiation emitted to the subject H such that radiation with intensity corresponding to predetermined imaging conditions is emitted to the subject H for only a set period of time. The imaging conditions include a tube voltage (kV value) and an mAs value (a tube current×an irradiation time) corresponding to the body thickness of the subject H. The body thickness of the subject H can be calculated by measuring a source image receptor distance (SID) which is the distance between the device 10 and the surface of the radiation detector 80 and a source object distance (SOD) which is the distance between the device 10 and the surface of the subject H, using the distance sensor 45, and subtracting the SOD from the SID. In addition, the operator may measure the body thickness and input information for setting the imaging conditions including the measured body thickness to the control device 23 through the input unit 26. In this exemplary embodiment, the information for setting the imaging conditions including, for example, the body thickness is transmitted to the console 90 and the imaging conditions are set in the console 90. The set imaging conditions are transmitted to the control device 23 of the radiation emitting device 10. The irradiation control unit 71 controls the emission of radiation to the subject H, using the imaging conditions transmitted from the console 90.

The imaging control unit 72 drives the camera 44 to capture an image of the surface of the subject H and acquires a captured image G1. In addition, the imaging control unit 72 may perform image processing for improving image quality for the captured image G1 acquired by the camera 44. The captured image G1 acquired by the camera 44 is a motion picture with a predetermined frame rate of, for example, 30 fps.

The control unit 73 controls the overall driving operation of the radiation emitting device 10. That is, the control unit 73 performs, for example, a process of instructing the irradiation control unit 71 to drive the radiation source 60, a process of instructing the collimator control unit 61 to drive the collimator 46, a process of instructing the imaging control unit 72 to drive the camera 44 such that the captured image G1 is acquired, a process of displaying various kinds of information including the captured image G1 on the monitor 25, a process of instructing the communication unit 74 to exchange various kinds of information with the console 90, a process of monitoring the state of the battery 75, a process of receiving a command from the input unit 26, a process of measuring the distance between the radiation emitting device 10 and an object using the distance sensor 45, a process of detecting the pivot angle of the radiation source unit 40 using the angle sensor 49, a process of detecting the movement of the radiation source unit 40 using the motion sensor 62. In addition, the control unit 73 performs a process of driving the motors 53 and 54 of the driving unit 50 to change the inclination and rotation angle of the monitor 25 on the basis of content displayed on the monitor 25 as described below. Furthermore, the control unit 73 performs a process which calculates the average value of the pixel values of each pixel in the captured image G1 as the brightness of the captured image G1 and changes the brightness of the monitor 25 according to the brightness. In this case, the control unit 73 performs a process which further increases the brightness of the monitor 25 in a case in which the captured image G1 is bright and decreases the brightness of the monitor 25 in a case in which the captured image G1 is dark. Each of the above-mentioned processes is performed by the commands from the input unit 26 or the commands that have been transmitted from the console 90 and received by the communication unit 74.

The input unit 26 is a touch-panel-type input unit that is integrated with the monitor 25, receives a command from the operator, and outputs information indicating the command to the control unit 73.

The communication unit 74 performs wireless communication with the console 90 to exchange information. In addition, the radiation emitting device 10 may be connected to the console 90 by a cable, instead of wireless communication, and may exchange information with the console 90 in a wired manner. In the latter case, the communication unit 74 has a connector to which the cable is connected.

Figure 9:
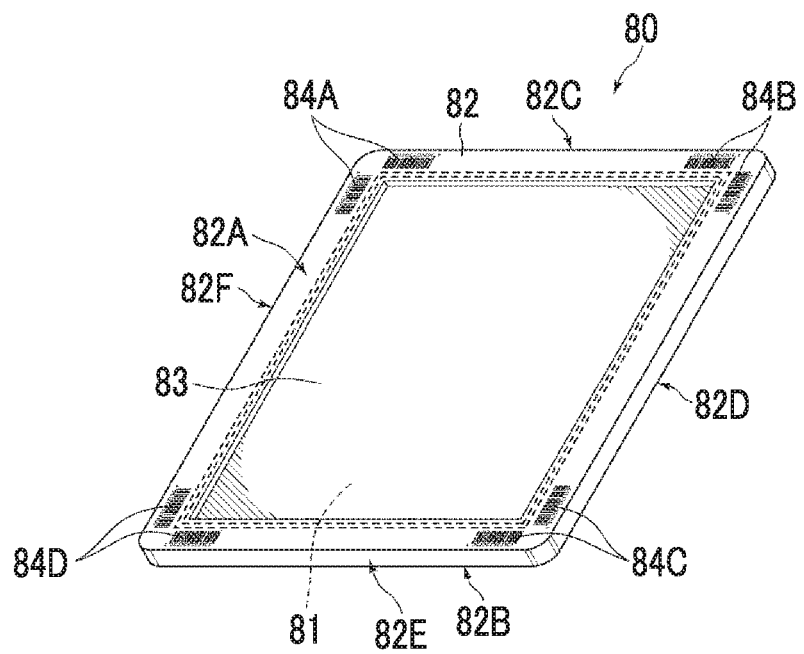
FIG. 9 is a perspective view illustrating the outward appearance of a radiation detector as viewed from a front surface which is the radiation emitting side.
Figure 10:
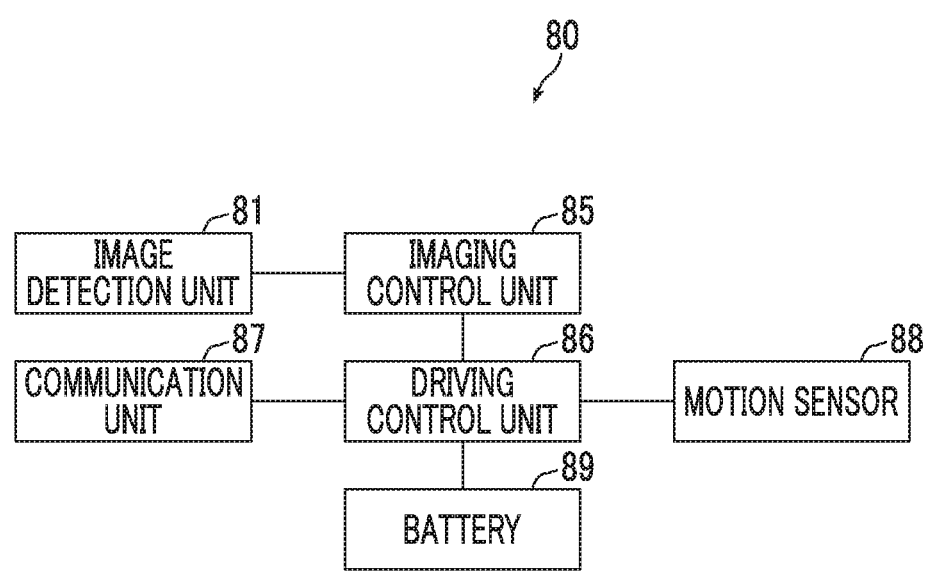
FIG. 10 is a block diagram schematically illustrating the internal configuration of the radiation detector.

Next, the configuration of the radiation detector 80 will be described below. FIG. 9 is a perspective view illustrating the outward appearance of the radiation detector as viewed from the front surface which is a radiation emitting side and FIG. 10 is a block diagram schematically illustrating the internal configuration of the radiation detector.

As illustrated in FIG. 9, the radiation detector 80 is a cassette-type radiation detector including a housing 82 that accommodates an image detection unit 81. The image detection unit 81 includes a scintillator (phosphor) that converts incident radiation into visible light and a thin film transistor (TFT) active matrix substrate, as known in the art. A rectangular imaging region in which a plurality of pixels that accumulate charge corresponding to the visible light from the scintillator are arranged is formed on the TFT active matrix substrate. The housing 82 includes, for example, an imaging control unit 85 including a gate driver that applies a gate pulse to a gate of a TFT to switch the TFT and a signal processing circuit that converts the charge accumulated in the pixel into an analog electric signal indicating an X-ray image and outputs the analog electric signal, in addition to the image detection unit 81.

The housing 82 has a rectangular parallelepiped shape having a front surface 82A on which radiation is incident, a rear surface 82B opposite to the front surface 82A, and four side surfaces 82C, 82D, 82E, and 82F. The housing 82 is made of, for example, a conductive resin and also functions as an electromagnetic shield that prevents the penetration of electromagnetic noise into the radiation detector 80 and the emission of electromagnetic noise from the inside of the radiation detector 80 to the outside. The housing 82 has a size that is based on International Organization for Standardization (ISO) 4090:2001 and is substantially equal to the size of, for example, a film cassette, an imaging plate (IP) cassette, or a computed radiography (CR) cassette. In this exemplary embodiment, the shape of the front surface 82A of the housing 82 is a rectangular shape having the side surfaces 82D and 82F as long sides.

A transmission plate 83 that transmits radiation is attached to the front surface 82A of the housing 82. The transmission plate 83 has a size that is substantially equal to the size of a radiation detection region of the radiation detector 80 and is made of a carbon material that has a small weight, high rigidity, and high transmittance. The shape of the detection region is a rectangular shape that is the same as the shape of the front surface 82A of the housing 82.

Markers 84A to 84D that indicate identification information for identifying the radiation detector 80 are attached to four corners of the front surface 82A of the housing 82. In this exemplary embodiment, each of the markers 84A to 84D includes two bar codes that are perpendicular to each other. The two bar codes are attached to the front surface 80A of the radiation detector 80 so as to define four corners of the detection region of the radiation detector 80. For example, a tape with a color unique to the radiation detector 80 may be used as the marker as long as it can identify the radiation detector 80. In this case, the radiation detector 80 can be identified by the colors of the markers.

Here, each of the markers 84A to 84D is a pair of two bar codes. However, in this exemplary embodiment, information indicating the vertical direction of the image detection unit 81 provided in the radiation detector 80 is included in one of the two bar codes. In this exemplary embodiment, the side to which the markers 84A and 84B are attached is an upper side, that is, a top side. Therefore, in this exemplary embodiment, in the radiation detector 80, in a case in which the side to which the markers 84A and 84B are attached and the side to which the markers 84C and 84D are attached are defined, a direction from the side to which the markers 84A and 84B are attached to the side to which the markers 84C and 84D are attached along a straight line perpendicular to the two sides is the vertical direction. The vertical direction means a direction on the radiation detector 80 and does not mean the direction of gravity.

In addition, a light emitting element, such as an LED that emits light with a color unique to the radiation detector 80, may be used as the marker. In this case, the radiation detector 80 can be identified by the color of the light emitting element. In addition, in a case in which a plurality of light emitting elements are used, the radiation detector 80 can be identified by the turn-on pattern or the blinking pattern of the light emitting elements.

The housing 82 includes an image detection unit 81, the imaging control unit 85, a driving control unit 86, a communication unit 87, a motion sensor 88, and a battery 89. The imaging control unit 85, the driving control unit 86, and the communication unit 87 are implemented by a program (software) that is operated in a computer, dedicated hardware, or a combination thereof. The program is installed in the radiation detector 80 as in the radiation emitting device 10.

As described above, the imaging control unit 85 includes, for example, the gate driver and the signal processing circuit, controls the driving of the gate driver and the signal processing circuit such that an analog image signal indicating a radiographic image G2 is generated and outputs the analog image signal to the driving control unit 86.

The driving control unit 86 controls the overall driving operation of the radiation detector 80. That is, the driving control unit 86 performs, for example, a process of instructing the imaging control unit 85 to generate an image signal indicating the radiographic image G2, a process of instructing the communication unit 87 to exchange the image signal indicating the radiographic image G2 and various kinds of information with the console 90, a process of detecting the movement of the radiation detector 80 using the motion sensor 88, and a process of monitoring the state of the battery 89.

The communication unit 87 performs wireless communication with the console 90 to exchange information. In addition, the radiation detector 80 may be connected to the console 90 by a cable, instead of wireless communication, and may exchange information with the console 90 in a wired manner. In the latter case, the communication unit 87 has a connector to which the cable is connected.

The motion sensor 88 is a 9-axis motion sensor that detects 3-axis acceleration, 3-axis angular velocity, and 3-axis tilt. The acceleration, angular velocity, and tilt detected by the motion sensor 88 are output as movement information to the driving control unit 86 and are transmitted from the communication unit 87 to the console 90.

Figure 11:
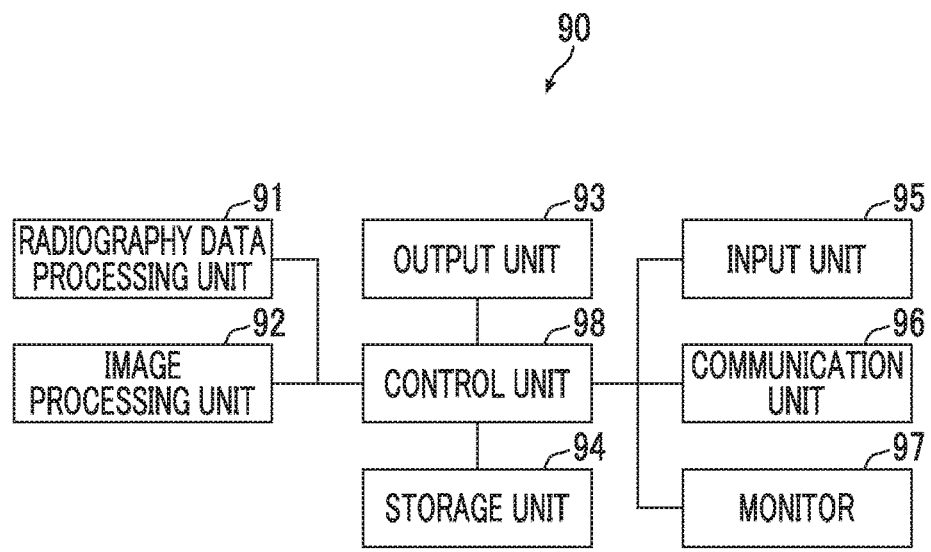
FIG. 11 is a block diagram schematically illustrating the internal configuration of a console.

FIG. 11 is a block diagram schematically illustrating the internal configuration of the console. As illustrated in FIG. 11, the console 90 includes a radiography data processing unit 91, an image processing unit 92, an output unit 93, a storage unit 94, an input unit 95, a communication unit 96, a monitor 97, and a control unit 98. The radiography data processing unit 91, the image processing unit 92, the communication unit 96, and the control unit 98 are implemented by a program (software) that is operated in a computer, dedicated hardware, or a combination thereof. The program is installed in the console 90 as in the control device 23 of the radiation emitting device 10.

The radiography data processing unit 91 performs data processing, such as A/D conversion, for the image signal indicating the radiographic image G2 of the subject H which has been input from the radiation detector 80. The radiography data processing unit 91 outputs radiographic image data indicating the digital radiographic image G2 subjected to the data processing.

The image processing unit 92 performs predetermined image processing for the radiographic image data output from the radiography data processing unit 91, using image processing parameters stored in the storage unit 94. Examples of the image processing performed by the image processing unit 92 include various types of image processing, such as image calibration (the correction of radiographic image data by calibration data) including pixel defect correction, a process of creating a defect map for performing the pixel defect correction, offset correction, gain correction using a predetermined uniformly exposed image, and shading correction, a gradation correction process, a density correction process, a process of removing scattered rays caused by radiation transmitted through the subject H, and data conversion for converting image data into data for monitor display or data for printout. The image processing unit 92 outputs radiographic image data subjected to the image processing.

The output unit 93 outputs the radiographic image data subjected to the image processing which has been input from the image processing unit 92. The output unit 93 is, for example, a printer that prints out a radiographic image or a storage device that stores radiographic image data.

The storage unit 94 stores, for example, the size of the detection region of the radiation detector 80, image processing parameters for image processing performed by the image processing unit 92, parameters corresponding to the type of the radiation detector 80 and the body thickness of the subject H for setting the imaging conditions, and various kinds of information required for processes in the console 90. In addition, the storage unit 94 stores, for example, the radiographic image G2 output from the image processing unit 92 and the captured image G1 transmitted from the radiation emitting device 10. The storage unit 94 may be a semiconductor memory or a recording medium such as a hard disk. In addition, the storage unit 94 may be provided in the console 90. Alternatively, the storage unit 94 may be provided outside the console 90, may be connected to the console 90, and may be used.

The input unit 95 is, for example, a keyboard for inputting various kinds of information to the console 90. In addition, the input unit 95 may be a touch panel.

The communication unit 96 performs wireless communication with the radiation emitting device 10 and the radiation detector 80 to exchange information. In addition, the console 90 may be connected to the radiation emitting device 10 and the radiation detector 80 by a cable, instead of wireless communication, and may exchange information with the radiation emitting device 10 and the radiation detector 80 in a wired manner. In the latter case, the communication unit 96 has a connector to which the cable is connected.

The monitor 97 is, for example, a liquid crystal panel and displays various kinds of information related to the console 90 and the radiographic image G2 transmitted from the radiation detector 80. In addition, the monitor 97 displays, for example, the captured image G1 if necessary.

The control unit 98 controls the overall driving operation of the console 90. That is, the control unit 98 performs, for example, a process of instructing the radiography data processing unit 91 to acquire the radiographic image G2, a process of instructing the image processing unit 92 to perform image processing for the radiographic image G2, a process of detecting the markers 84A to 84D of the radiation detector 80 from the captured image G1, a process of detecting the identification information of the radiation detector 80 and the direction of the radiation detector 80 from any one of the detected markers 84A to 84D, a process of outputting the radiographic image G2 to the output unit 93, a process of acquiring the inclination of the radiation detector 80 from the movement information of the radiation detector 80 acquired by the motion sensor 88 of the radiation detector 80 and acquiring the rotation angle and direction of the radiation detector 80 from the movement information if necessary, a process of instructing the communication unit 96 to exchange various kinds of information with the radiation emitting device 10 and the radiation detector 80, a process of receiving commands from the input unit 95, and a process of displaying various kinds of information on the monitor 97.

Here, the inclination of the radiation detector 80 means a two-dimensional inclination with respect to a horizontal plane parallel to the detection surface in a state in which the radiation detector 80 is kept horizontal. In a case in which the x-axis and the y-axis are set on the detection surface of the radiation detector 80, the inclination of the radiation detector 80 is the inclination angle of radiation detector 80 about each of the x-axis and the y-axis with respect to the horizontal plane. In a case in which an image of the subject H is captured, the direction of each side of the radiation detector 80 included in the captured image G1 is generally aligned with the direction of each side of the captured image G1. Therefore, the x-axis and the y-axis on the radiation detector 80 vary depending on the directions included in the captured image G1. In this exemplary embodiment, the x-axis of the radiation detector 80 is aligned with the left-right direction of the captured image G1 and the y-axis is aligned with the up-down direction of the captured image G1.

The rotation angle of the radiation detector 80 is the angle of rotation on an axis perpendicular to the detection surface of the radiation detector 80. Specifically, the rotation angle means an angle at which the radiation detector 80 is disposed so as to be vertically long and is then used and an angle at which the radiation detector 80 is disposed so as to be horizontally long and is then used.

The direction of the radiation detector 80 is the vertical direction from a lower portion to an upper portion of the detection surface of the radiation detector 80 in this exemplary embodiment. As described above, in the this exemplary embodiment, since the side on which the markers 84A and 84B are attached is the upper side, that is, the top side, a direction to a portion in which the markers 84A and 84B are attached in the direction of the long axis of the radiation detector 80 is the vertical direction. In addition, other directions may be used as the direction of the radiation detector 80. For example, a direction perpendicular to the vertical direction may be used.

Figure 12:
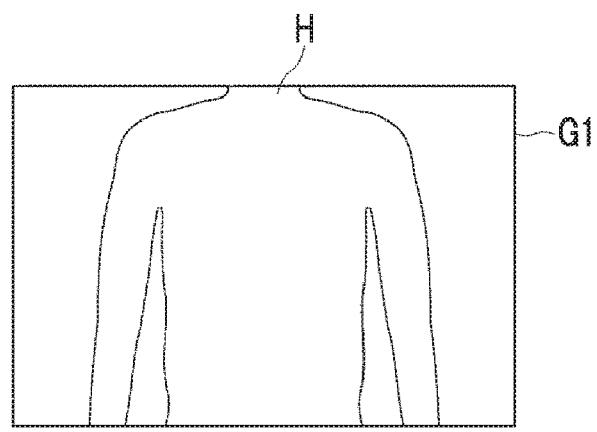
FIG. 12 is a diagram illustrating a captured image including only a subject.
Figure 13:
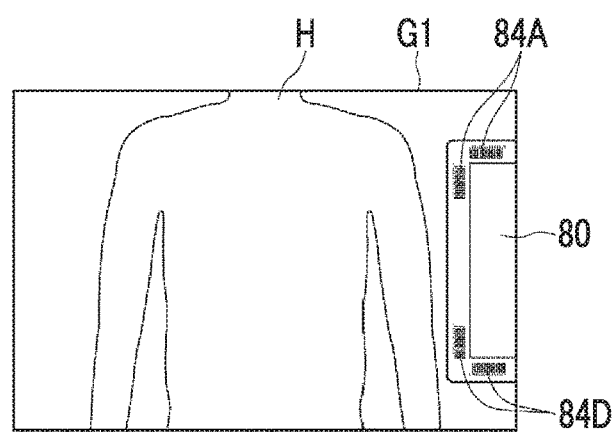
FIG. 13 is a diagram illustrating a captured image including a portion of the radiation detector in addition to the subject.

Next, the detection of the radiation detector 80 in the captured image G1 will be described. In a case in which a radiographic image of the subject H is acquired, the operator extends the arm portion 30 and sets the length of the arm portion 30 and the pivot position of the radiation source unit 40 on the upper side of the subject H such that the radiation source unit 40 is located immediately above the subject H. Then, an image of the subject H is captured by the camera 44 of the radiation source unit 40. In this exemplary embodiment, it is assumed that an image of the chest of the subject H is captured. Therefore, before imaging, the chest of the subject H is included in the captured image G1 as illustrated in FIG. 12. Then, in a case in which an operation of inserting the radiation detector 80 between the bed 2 and the subject H is performed in order to acquire the radiographic image G2 of the subject H, a portion of the radiation detector 80 is included in the captured image G1 as illustrated in FIG. 13. Here, the markers 84A to 84D are attached to four corners of the radiation detector 80. The control unit 98 detects whether the captured image G1 includes any one of the markers 84A to 84D. In a case in which it is detected that the captured image G1 includes any one of the markers 84A to 84D, the control unit 98 determines that the radiation detector 80 is included in the captured image G1.

The control unit 98 transmits radiation detector position information indicating the position of the radiation detector 80 in the captured image G1 from the communication unit 96 to the radiation emitting device 10. The radiation detector position information is a coordinate position indicating the position of the corners of the detection region of the radiation detector 80 on the captured image G1. In this exemplary embodiment, the size of the detection region of the radiation detector 80 is stored in the storage unit 94 in advance. The control unit 98 calculates the radiation detector position information from the position of any one of the markers 84A to 84D which has been detected from the captured image G1 and the size of the detection region. In addition, in a case in which the radiation detector position information has been known, it is possible to calculate the information of the position of the center of the radiation detector 80 from the size of the detection region of the radiation detector 80. Therefore, the control unit 98 also transmits center position information indicating the position of the center of the radiation detector 80 to the radiation emitting device 10. In addition, the control unit 98 recognizes the vertical direction of the radiation detector 80 from any one of the markers 84A to 84D and also transmits the information of the vertical direction to the radiation emitting device 10. Furthermore, the control unit 98 transmits inclination information indicating the inclination of the radiation detector 80 to the radiation emitting device 10. In addition, the control unit 98 transmits rotation angle information indicating the rotation angle of the radiation detector 80 to the radiation emitting device 10 if necessary.

Figure 14:
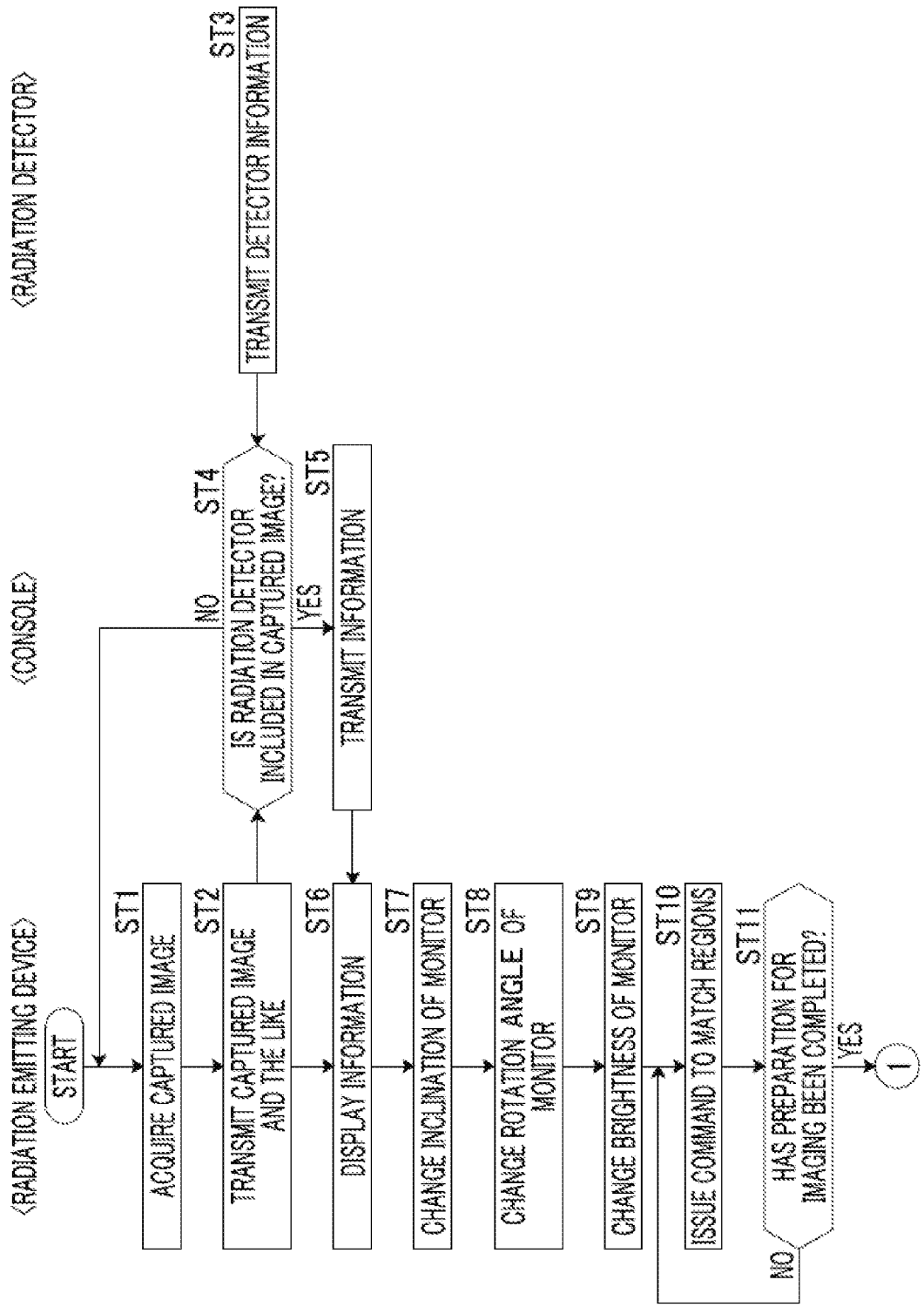
FIG. 14 is a flowchart illustrating a process performed in this exemplary embodiment.
Figure 15:
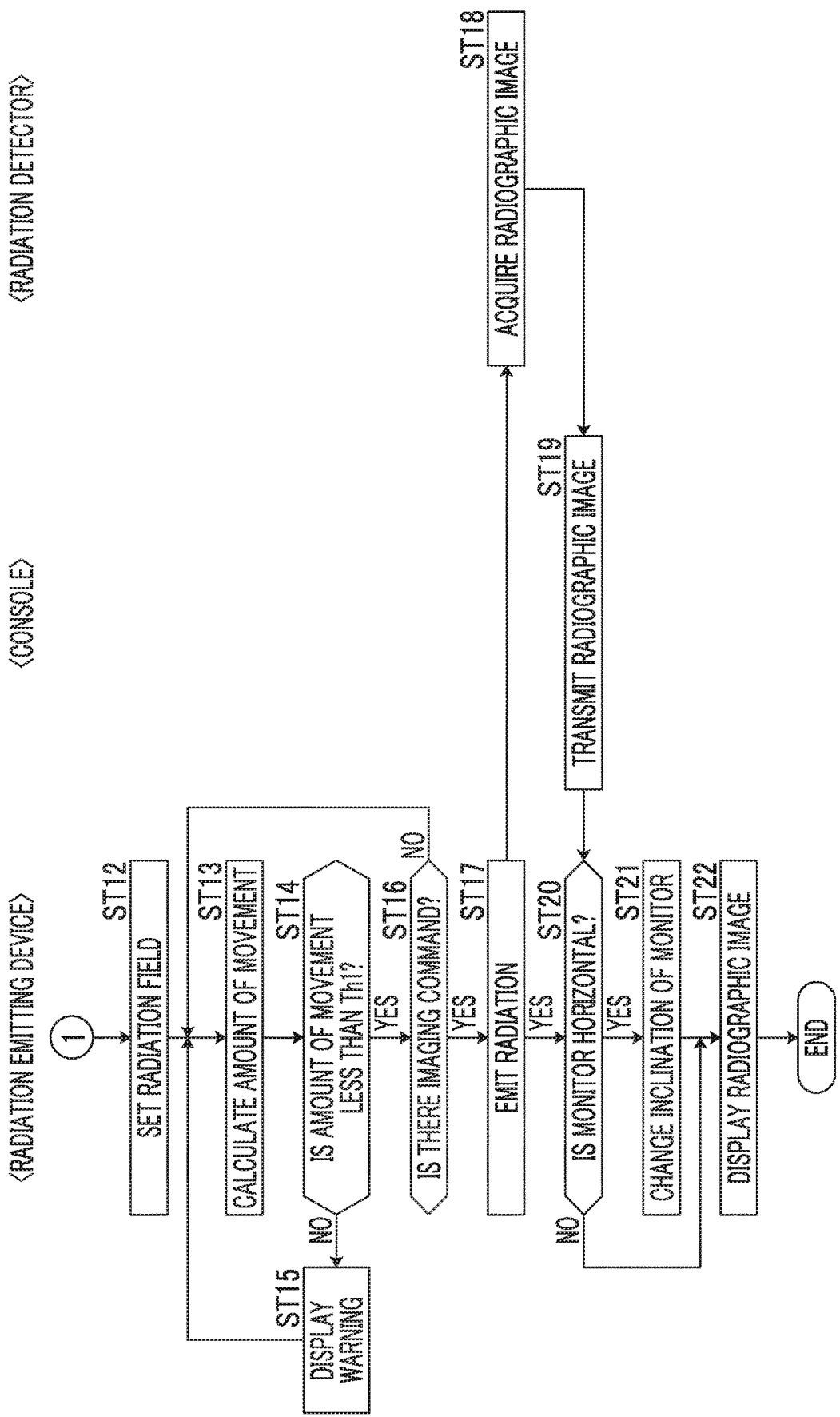
FIG. 15 is a flowchart illustrating a process performed in this exemplary embodiment.

Next, a process performed in this exemplary embodiment will be described. FIGS. 14 and 15 are flowcharts illustrating the process performed in this exemplary embodiment. In the radiography apparatus according to this exemplary embodiment, it is assumed that two operators handle the radiation emitting device 10 and the radiation detector 80 to perform a pre-imaging operation for positioning the radiation detector 80 behind the subject H or setting the radiation field and perform an imaging operation after the pre-imaging operation is completed. In addition, one operator may perform the same operation as described above. Furthermore, it is assumed that, before the pre-imaging operation, the monitor 25 is in the initial state illustrated in FIG. 1, that is, a state in which the monitor 25 is horizontally long and the inclination of the monitor 25 with respect to the horizontal plane is 0 degrees.

Figure 16:
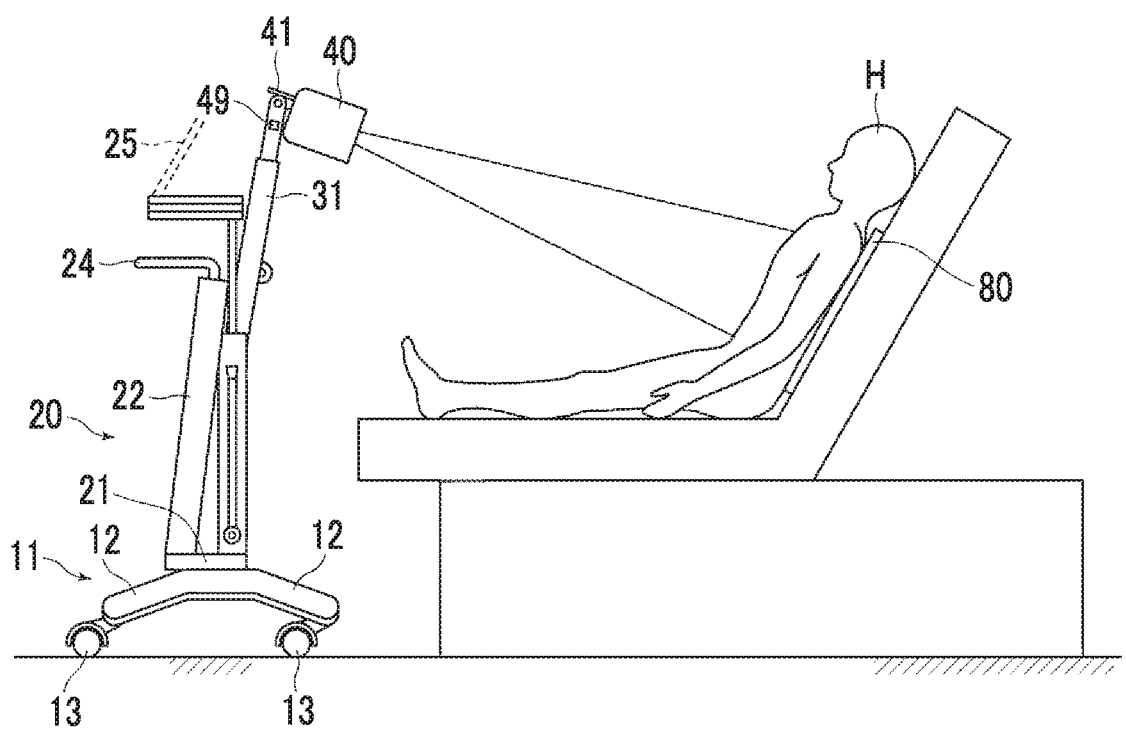
FIG. 16 is a diagram illustrating a situation in which an image of the subject whose upper body is raised is captured.

Here, in a case in which an image of the subject H that lies on the bed 2 as illustrated in FIG. 2 is captured, the direction of the radiation source unit 40 is set such that the radiation source unit 40 directly faces the subject H. In this case, the pivot angle is 0 degrees. In contrast, in a case in which an image of the subject H whose upper body is raised as illustrated in FIG. 16, the direction of the radiation source unit 40 is set such that the radiation source unit 40 obliquely faces subject H. In this case, the pivot angle is in the range of 0 degrees to 90 degrees. Therefore, in this exemplary embodiment, the operator unlocks the lock lever 41 to adjust the pivot angle of the radiation source unit 40 such that the radiation source unit 40 is aligned with a desired direction. In a case in which the radiation source unit 40 is adjusted to the desired, the radiation source unit 40 is fixed to the desired direction by the lock lever 41. In this exemplary embodiment, it is assumed that an image of the subject H whose upper body is raised as illustrated in FIG. 16 is captured.

In this state, the camera 44 captures an image of the subject H and the captured image G1 of the subject H is acquired (Step ST1). The radiation emitting device 10 transmits the captured image G1, the SID, the SOD, and the information of the radiation field defined by the collimator 46 to the console 90 (the transmission of, for example, the captured image: Step ST2). In addition, the radiation detector 80 transmits, for example, information indicating the driving state of the radiation detector 80, information indicating the remaining battery level of the radiation detector 80, and the movement information detected by the motion sensor 88 to the console 90 (the transmission of detector information: Step ST3).

The control unit 98 of the console 90 determines whether the radiation detector 80 is included in the captured image G1 (Step ST4). In a case in which the determination result in Step ST4 is "NO", the process returns to Step ST1. In a case in which the process returns to Step ST1, the transmission of the detector information in Step ST3 may be omitted. In a case in which the determination result in Step ST4 is "YES", the control unit 98 acquires information related to the detector which includes the identification information of the radiation detector 80, radiation detector position information indicating the position of the radiation detector 80 on the captured image G1, information indicating the vertical direction of the radiation detector 80, and the center position information of the radiation detector 80, on the basis of any one of the markers 84A to 84D of the radiation detector 80 included in the captured image G1. In addition, the control unit 98 subtracts the SOD from the SID to calculate the body thickness of the subject H and sets imaging conditions from the body thickness. The control unit 98 acquires the inclination information of the radiation detector 80 from the movement information of the radiation detector 80.

In addition, the imaging conditions may be set according to a part of the subject H included in the captured image G1. Information about the part of the subject H may be input to the radiation emitting device 10 by the operator and acquired. Alternatively, the information may be input through the input unit 95 of the console 90 and acquired. In addition, an appropriate quality of radiation (whether the voltage is high or low) varies depending on the type of scintillator used in the image detection unit 81 provided in the radiation detector 80. Therefore, the imaging conditions may be set according to the material forming the scintillator used in the image detection unit 81 provided in the radiation detector 80, in addition to the body thickness. In this case, the storage unit 94 may store a table in which the information of the scintillator used in the image detection unit 81 and the imaging conditions, which correspond to the identification information of the radiation detector 80, are associated with each other. In this case, it is possible to set the imaging conditions corresponding to the identification information of the radiation detector 80 acquired from the captured image G1 with reference to the table. In addition, in a case in which imaging information obtained when an image of the same subject H is captured using the same radiation emitting device 10 and the same radiation detector 80 has been stored, the imaging conditions may be set, considering the imaging information.

Figure 17:
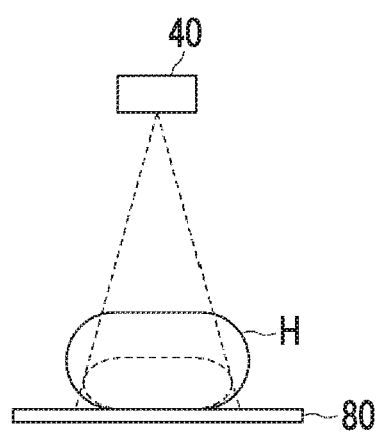
FIG. 17 is a diagram illustrating a change in a radiation field depending on the body thickness of the subject.

Here, the size of the field of the radiation emitted from the radiation emitting device 10 is different in a case in which the body thickness of the subject H is large and in a case in which the body thickness of the subject H is small, as illustrated in FIG. 17. Specifically, as the body thickness decreases, the radiation field increases. Therefore, the control unit 98 calculates the body thickness of the subject H from the SID and the SOD and acquires information related to the radiation field which includes information about the size and the position of the center of a radiation field region, on the basis of the information of the range defined by the collimator 46 which has been transmitted from the radiation emitting device 10. Then, the control unit 98 transmits the identification information, the detector information, the information related to the detector, the information related to the radiation field, the imaging conditions, and the inclination information of the radiation detector 80 to the radiation emitting device 10 (the transmission of information: Step ST5).

In contrast, in a case in which the radiation detector 80 is moved after the radiation detector 80 is included in the captured image G1, the radiation detector 80 is moved to a position out of the angle of view of the camera 44 and the radiation detector 80 may not be included in the captured image G1. In addition, in a case in which the radiation detector 80 is completely hidden by the subject H, the radiation detector is not included in the captured image G1. In this case, since the markers 84A to 84D are not included in the captured image G1, it is difficult to specify, for example, the position of the radiation detector 80 from only the captured image G1.

Therefore, in this exemplary embodiment, in a case in which the radiation detector 80 is not included in the captured image G1, the control unit 98 acquires the movement information of the radiation detector 80 detected by the motion sensor 88. Then, the control unit 98 calculates the amount of movement of the radiation detector 80 from a reference position which is the position of any one of the markers 84A to 84D of the radiation detector 80 in a case in which any one of the markers 84A to 84D of the radiation detector 80 is included in the captured image G1, on the basis of the movement information and the size of the detection region of the radiation detector 80. Then, the control unit 98 acquires radiation detector position information on the basis of the calculated amount of movement. In this way, even in a case in which the radiation detector 80 is not included in the captured image G1, it is possible to track the position of the radiation detector 80.

The control unit 73 of the radiation emitting device 10 displays the identification information of the radiation detector 80, the driving state of the radiation detector 80, the vertical direction of the radiation detector 80, the remaining battery level of the radiation detector 80, the inclination of the radiation detector 80, a region corresponding to the radiation detector 80, the position of the center of the radiation detector 80, and the radiation field defined by the collimator 46 so as to be superimposed on the captured image G1 displayed on the monitor 25, on the basis of the information transmitted from the console 90 (the display of information: Step ST6).

Figure 18:
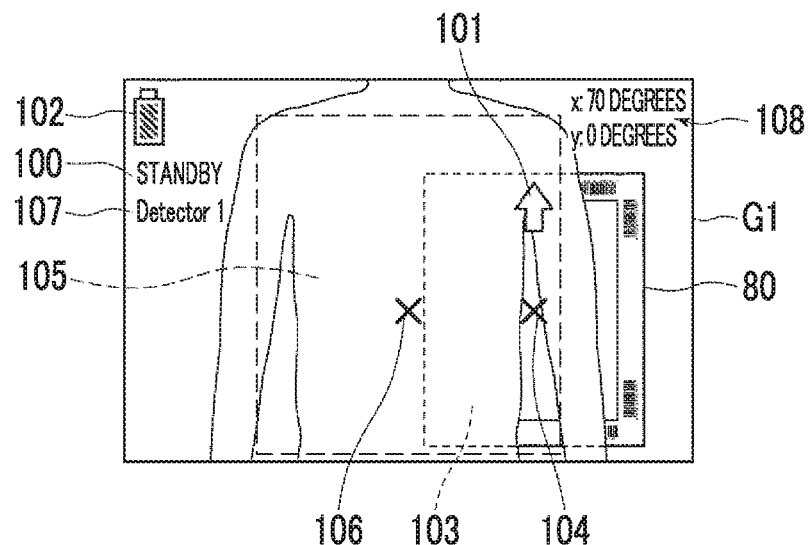
FIG. 18 is a diagram illustrating a captured image on which various kinds of information are superimposed.

FIG. 18 is a diagram illustrating the captured image G1 on which various kinds of information are superimposed. As illustrated in FIG. 18, a text (here, "standby") 100 indicating the driving state of the radiation detector 80, an arrow 101 indicating the vertical direction of the radiation detector 80, an icon 102 indicating the remaining battery level of the radiation detector 80, a detection region 103 corresponding to the detection region of the radiation detector 80, a center position 104 of the radiation detector 80, a radiation field region 105, a center position 106 of the radiation field region 105, a text 107 "Detector1" which is the identification information of the radiation detector 80, and the inclination 108 of the radiation detector 80 are displayed on the captured image G1 displayed on the monitor 25 so as to be superimposed thereon. It is preferable that the detection region 103 and the radiation field region 105 are displayed so as to be distinguished from each other. For example, it is preferable that the color of the detection region 103 is different from the color of the radiation field region 105. The colors may be designated by a command from the console 90.

In the console 90, it is preferable that the control unit 98 detects the color of the clothes of the subject H from the captured image G1 and designates the colors of the detection region 103 and the radiation field region 105 so as to be different from the color of the clothes. In this case, it is possible to prevent the confusion between the color of the clothes of the subject H and the colors of the detection region 103 and the radiation field region 105 superimposed on the captured image G1.

Figure 19:
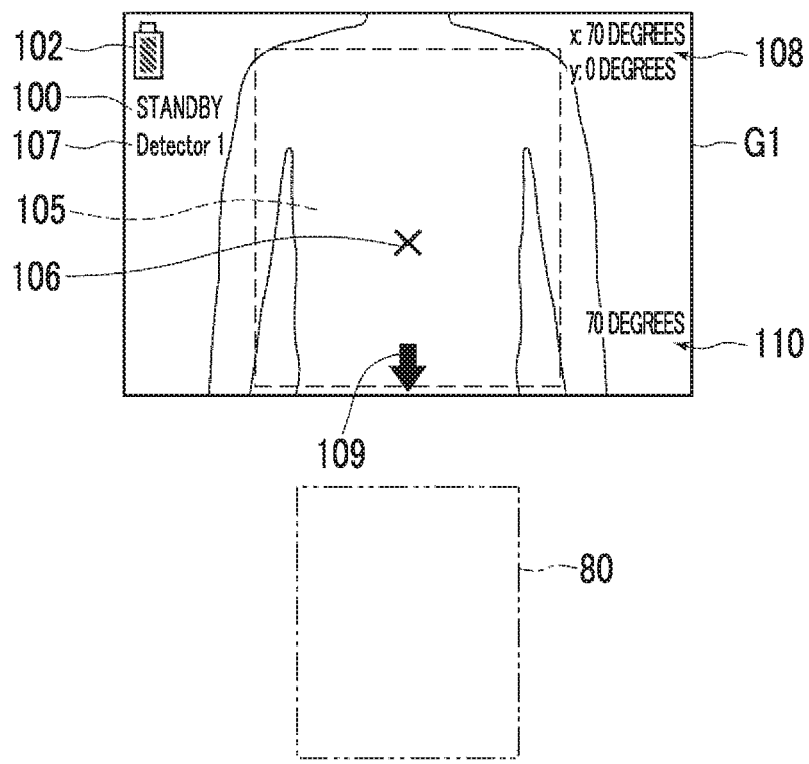
FIG. 19 is a diagram illustrating a captured image on which information indicating a direction in which the radiation detector is present is superimposed.

In a case in which the radiation detector 80 is included in the captured image G1 and is then excluded from the captured image G1, information indicating the direction in which the radiation detector 80 is present may be displayed in the captured image G1, using the radiation detector position information calculated on the basis of the movement information of the radiation detector 80. FIG. 19 is a diagram illustrating a captured image on which the information indicating the direction in which the radiation detector 80 is present is superimposed, in addition to various kinds of information. In FIG. 19, the position of the radiation detector 80 is represented by a virtual line. As illustrated in FIG. 19, in addition to the information superimposed on the captured image G1 illustrated in FIG. 18, an arrow 109 as information indicating the direction in which the radiation detector 80 is present is displayed on the captured image G1 displayed on the monitor 25. In addition, instead of the arrow 109, letters indicating, for example, the up, down, left, and right sides may be used as the information indicating the direction in which the radiation detector 80 is present. Even in a case in which the radiation detector 80 is completely hidden behind the subject H, it is possible to specify the position of the radiation detector 80 in the captured image G1, using the radiation detector position information calculated on the basis of the movement information of the radiation detector 80. Therefore, it is possible to display the detection region 103 on the captured image G1.

In a case in which the inclination 108 of the radiation detector 80 is superimposed on captured image G1, the control unit 73 drives the motor 53 of the driving unit 50 to change the inclination of the support plate 52, thereby changing the inclination of the monitor 25 (Step ST7). At that time, the inclination angle of the support plate 52 is substantially equal to the inclination angle of the radiation detector 80 about the x-axis. In this exemplary embodiment, in a case in which the angle about the x-axis is 70 degrees as illustrated in FIG. 18, the motor 53 is driven such that the inclination of the monitor 25 with respect to the horizontal plane is 70 degrees. With this configuration, the monitor 25 is inclined with respect to the horizontal plane as illustrated in FIG. 16.

In this exemplary embodiment, in a case in which the subject H lies as illustrated in FIG. 2, the inclination of the radiation detector 80 with respect to the horizontal plane which has been detected on the basis of the movement information detected by the motion sensor 88 of the radiation detector 80 is 0 degrees. Therefore, the monitor 25 is kept in the horizontal state illustrated in FIG. 1. However, in a case in which the radiation detector 80 is inserted between a cushion of the bed 2 and the subject H, in some cases, the radiation detector 80 is inclined. In this case, the inclination of the radiation detector 80 which has been detected on the basis of the movement information detected by the motion sensor 88 of the radiation detector 80 is displayed on the monitor 25 so as to be superimposed on the captured image G1 and the inclination of the monitor 25 is changed on the basis of the display of the inclination of the monitor 25. In addition, the inclination angle of the monitor 25 may be a predetermined inclination angle. In a case in which the angle of the radiation detector 80 about the x-axis is 0 degrees, the monitor 25 is kept horizontal.

Figure 20:
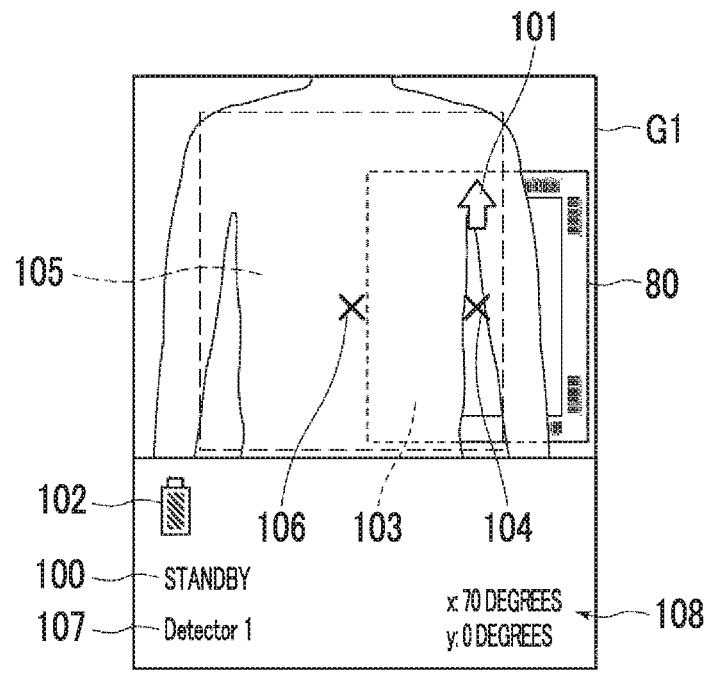
FIG. 20 is a diagram illustrating the display content of a monitor in a case in which the monitor is changed to a rotation angle at which the monitor is vertically long.

The control unit 73 changes the rotation angle of the monitor 25 according to the vertical direction of the radiation detector 80 (Step ST8). In this exemplary embodiment, the vertical direction of the radiation detector 80 is a direction from the lower side to the upper side of the direction in which the long axis of the radiation detector 80 is present. In a case in which the vertical direction of the radiation detector 80 is the upward direction of the captured image G1 as represented by an arrow 101 in FIG. 18, the radiation detector 80 is included in the captured image G1 so as to be vertically long. As such, in a case in which the vertical direction of the radiation detector 80 is the up-down direction of the captured image G1, the control unit 73 drives the motor 54 of the driving unit 50 to rotate the support plate 52 by 90 degrees in the counterclockwise direction such that the monitor 25 is rotated by 90 degrees in the counterclockwise direction and the rotation angle of the monitor 25 is changed to a value at which the monitor 25 is vertically long. In addition, the control unit 73 changes various kinds of information displayed on the monitor 25 according to the rotation angle of the monitor 25 in synchronization with the rotation of the monitor 25. FIG. 20 is a diagram illustrating the display content of the monitor 25 in a case in which the monitor 25 is at the rotation angle at which the monitor 25 is vertically long. In a case in which the vertical direction of the radiation detector 80 is the left-right direction of the captured image G1, the monitor 25 is maintained in a horizontally long state.

The control unit 73 calculates the average value of the pixel values of each pixel in the captured image G1 as the brightness of the captured image G1 and changes the brightness of the monitor 25 according to the brightness (Step ST9). That is, the control unit 73 performs a process which further increases the brightness of the monitor 25 in a case in which the captured image G1 is bright and decreases the brightness of the monitor 25 in a case in which the captured image G1 is dark. In a case in which the brightness of the captured image G1 is less than a predetermined threshold value, an imaging environment is dark. Therefore, in this case, the control unit 73 may reverse the light and dark of the captured image G1 and display the captured image G1 on the monitor 25, instead of changing the brightness.

As such, in a case in which the inclination, rotation angle, and brightness of the monitor 25 are changed, the operator adjusts the pivot angle of the radiation source unit 40 according to the inclination of the monitor 25. At that time, the direction of the radiation source unit 40 is adjusted such that the pivot angle is equal to the angle of the radiation detector 80 about the x-axis which is displayed on the monitor 25. Therefore, it is preferable to display a pivot angle 110 of the radiation source unit 40 measured by the angle sensor 49 on the monitor 25 as illustrated in FIG. 19. As such, the direction of the radiation source unit 40 is adjusted such that the emission axis of the radiation emitted from the radiation source unit 40 is perpendicular to the detection surface of the radiation detector 80.

Figure 21:
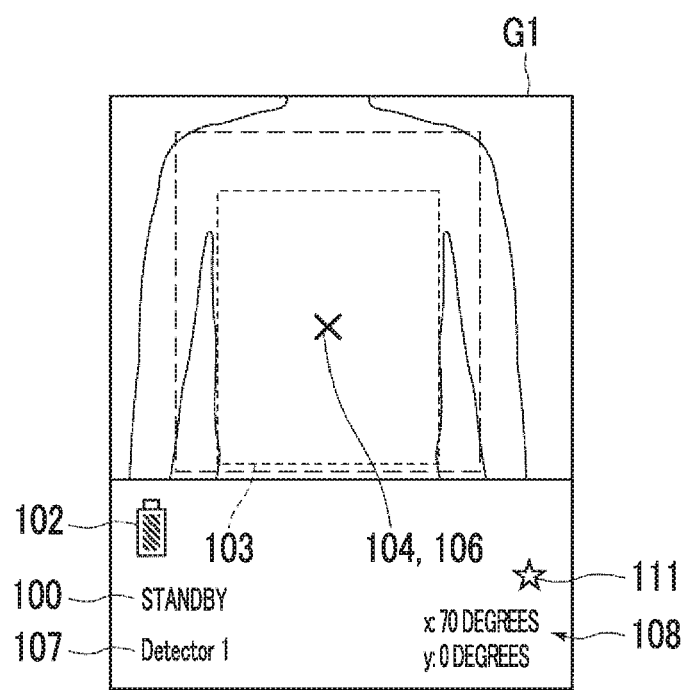
FIG. 21 is a diagram illustrating a state in which the position of the center of a radiation field region is matched with the position of the center of a detection region.

The operators of the radiation emitting device 10 and the radiation detector 80 perform a pre-imaging operation in cooperation with each other. That is, the operator of the radiation detector 80 moves the radiation detector 80 to an appropriate position behind the subject H and the operator of the radiation emitting device 10 checks whether the radiation detector 80 has been moved to the appropriate position while seeing the image displayed on the monitor 25. In addition, the operator moves the position of the radiation emitting device 10 if necessary. As illustrated in FIG. 21, the center position 106 of the radiation field region 105 and the center position 104 of the detection region 103 can be aligned with each other by this operation.

Furthermore, the control unit 98 may determine whether the center position of the radiation detector 80 has been aligned with the center position 106 of the radiation field region 105. In a case in which the positions have been aligned with each other, the control unit 98 may transmit information indicating the alignment to the radiation emitting device 10. In a case in which the information indicating the alignment is received, the radiation emitting device 10 displays information indicating that the center positions have been aligned with each other, such as a text "the center positions have been aligned with each other" or a mark indicating that the center positions have been aligned with each other, on the monitor 25. In FIG. 21, a star-shaped mark 111 indicates that the center positions have been aligned with each other. In addition, instead of displaying the text or the mark on the monitor 25, any method may be used as long as it can inform the operator that the center position of the radiation detector 80 has been aligned with the center position 106 of the radiation field region 105. For example, a method that outputs sounds or a method that blinks the monitor 25 may be used.

Here, in the state illustrated in FIG. 21, since the radiation field region 105 is larger than the detection region 103, it is difficult to change a radiation component that is emitted to the radiation detector 80 among the radiation components transmitted through the subject H into an image and the radiation component is unnecessary. The irradiation of the subject H with the unnecessary radiation component causes an increase in the amount of radiation exposure to the subject H.

Figure 22:
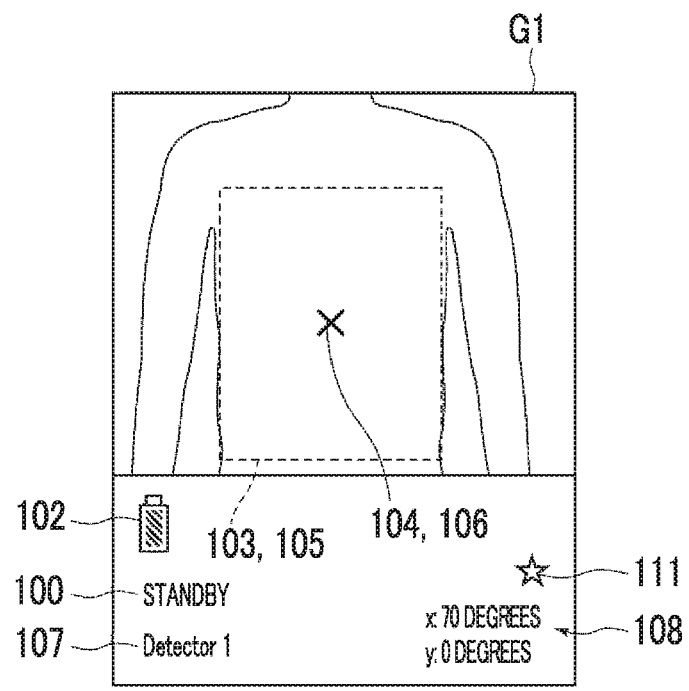
FIG. 22 is a diagram illustrating a state in which the radiation field region is matched with the detection region.

For this reason, the operator of the radiation emitting device 10 inputs a command to match the radiation field region 105 with the detection region 103 using the input unit 26 (the instruction of the matching between the regions: Step ST10). The command to match the regions is a command that is input by the operation of the radiation field region 105 displayed on the monitor 25 by, for example, the finger of the operator to match the radiation field region 105 with the detection region 103, as illustrated in FIG. 22. The collimator control unit 61 may drive the collimator 46 in operative association with the command to match the regions. In a case in which the collimator control unit 61 drives the collimator 46 whenever the command to match the radiation field region 105 with the detection region 103 is issued, power consumption increases. For this reason, in this exemplary embodiment, the collimator control unit 61 may drive the collimator 46 in a case in which the issuing of the command to match the radiation field region 105 with the detection region 103 through the input unit 26 ends and the input unit 26 receives input information indicating that preparation for imaging has been completed.

The control unit 73 of the radiation emitting device 10 determines whether the preparation for imaging has been completed (Step ST11). As described above, information indicating that the preparation for imaging has been completed may be received from the input unit 26. In a case in which the determination result in Step ST11 is "NO", the process returns to Step ST10.

In a case in which the determination result in Step ST11 is "YES", the control unit 73 turns on the radiation field lamp 63 and directs the collimator control unit 61 to drive the collimator 46 such that the radiation field is set (Step ST12). At that time, it is preferable to notify the operator that the collimator 46 is being driven by, for example, blinking the radiation field region 105 displayed on the monitor 25. In addition, the control unit 73 of the radiation emitting device 10 does not receive the input of an imaging command while the collimator 46 is being driven. Then, in a case in which the driving of the collimator 46 is completed, the control unit 73 detects the movement of the radiation emitting device 10, using the motion sensor 62, and calculates the amount of movement of the radiation emitting device 10 per unit time (Step ST13). The amount of movement of the radiation emitting device 10 per unit time corresponds to the shaking of the hand of the operator. The control unit 73 determines whether the amount of movement per unit time is less than a threshold value Th1 (Step ST14). In a case in which the determination result in Step ST14 is "NO", the control unit 73 displays a warning on the monitor 25 (Step ST15) and returns to Step ST13. For example, the operator can take an action of firmly holding the radiation emitting device 10 in response to the displayed warning.

In a case in which the determination result in Step ST14 is "NO", the control unit 73 controls the radiation source 60 such that radiation is not emitted even in a case in which an imaging command is received from the input unit 26. Instead of this configuration, for example, the input of the imaging command from the input unit 26 may be disabled. In addition, the threshold value Th1 may change depending on the radiation emission time included in the imaging conditions. For example, in a case in which the radiation emission time is long, the influence of hand shaking increases. Therefore, the threshold value Th1 may be changed such that it decreases as the radiation emission time increases.

In a case in which the determination result in Step ST14 is "YES", the control unit 73 determines whether an imaging operation has been input from the input unit 26 (Step ST16). In a case in which the determination result in Step ST16 is "NO", the process returns to Step ST13. In a case in which the determination result in Step ST16 is "YES", the control unit 73 drives the radiation source 60 such that radiation is emitted to the subject H and the subject H is irradiated with the radiation (Step ST17). In a case in which the determination result in Step ST14 is "YES", the control unit 73 may display information indicating that imaging can be performed on the monitor 25. In a case in which the determination result in Step ST14 changes from "NO" to "YES", the control unit 73 stops the display of the warning on the monitor 25 such that the radiation source 60 can be driven in response to the imaging command from the input unit 26. In addition, in a case in which the input of an imaging command from the input unit 26 is disabled, the control unit 73 performs control such that the input of an imaging command from the input unit 26 is enabled.

The radiation detector 80 detects the radiation transmitted through the subject H and acquires the radiographic image G2 of the subject H (Step ST18). The acquired radiographic image G2 is transmitted to the console 90 and the image processing unit 92 performs image processing for improving image quality and outputs the radiographic image G2 to the output unit 93. The control unit 98 transmits the radiographic image G2 subjected to the image processing to the radiation emitting device 10 (Step ST19).

The control unit 73 of the radiation emitting device 10 determines whether the monitor 25 is in a horizontal state (Step ST20). In a case in which the determination result in Step ST20 is "NO", the process proceeds to Step ST22. In a case in which the determination result in Step ST20 is "YES", the control unit 73 drives the motor 53 of the driving unit 50 to change the inclination angle of the monitor 25 to a predetermined value since the monitor 25 is in the horizontal state (Step ST21). The radiographic image G2 is displayed on the inclined monitor 25 (Step ST22) and the process ends. In this case, the captured image G1 and the radiographic image G2 may be displayed on the monitor 25 so as to be superimposed on each other or only the radiographic image G2 may be displayed on the monitor 25. In this way, it is possible to determine whether the radiographic image G2 has been appropriately acquired.

In some cases, the captured image G1 and the radiographic image G2 are displayed side by side. In addition, in some cases, a plurality of radiographic images G2 of the same subject H acquired at different dates and times are displayed side by side. In this case, the control unit 73 of the radiation emitting device 10 determines whether the rotation angle of the monitor 25 is a rotation angle at which the monitor 25 is horizontally long. In a case in which the monitor 25 is at a rotation angle at which the monitor 25 is vertically long, the control unit 73 changes the rotation angle of the monitor 25 such that the monitor 25 is horizontally long.

As such, in this exemplary embodiment, at least one of the inclination or the rotation angle of the monitor 25 is changed according to the display content of the monitor 25. Therefore, it is possible to change at least one of the inclination or the rotation angle of the monitor 25 according to the usage state of the device 10 and thus to improve the usability of the radiation emitting device 10. In addition, the brightness of the monitor 25 is controlled on the basis of the brightness of the captured image G1 displayed on the monitor 25. Therefore, in a bright environment in which the captured image G1 is bright, it is possible to increase the brightness of the monitor 25. In a dark environment in which the captured image G1 is dark, it is possible to decrease the brightness of the monitor 25. As a result, it is possible to improve the usability of the radiation emitting device 10.

In a case in which the radiographic image G2 is displayed on the monitor 25, the inclination of the monitor 25 is changed such that the radiographic image G2 can be easily seen. In addition, in a case in which the captured image G1 and the radiographic image G2 are displayed side by side or a plurality of radiographic images G2 are displayed, the rotation angle of the monitor 25 is changed such that the monitor 25 is horizontally long. Therefore, a plurality of images can be displayed side by side in the horizontal direction. As a result, a plurality of images can be easily seen.

In the above-described exemplary embodiment, the radiation emitting device 10 and the radiation detector 80 are connected to the console 90 and the console 90 performs, for example, a process of setting imaging conditions and a process of performing image processing for the radiographic image. However, the functions of the console 90 may be performed by the control device 23 of the radiation emitting device 10. In this case, the radiation emitting device 10 and the radiation detector 80 may be directly connected to each other and may exchange various kinds of information. In this case, the control device 23 is implemented by a program, dedicated hardware, or a combination of the program and the dedicated hardware for implementing various processes of the console 90 in addition to various processes of the radiation emitting device 10. With this configuration, it is not necessary to install the console 90 in, for example, a hospital room. Therefore, it is possible to easily create an environment for capturing a radiographic image.

In the above-described exemplary embodiment, the vertical direction of the radiation detector 80 is recognized from any one of the markers 84A to 84D of the radiation detector 80 included in the captured image G1. However, the vertical direction of the radiation detector 80 may be recognized from the movement information of the radiation detector 80 detected by the motion sensor 88 of the radiation detector 80.

In the above-described exemplary embodiment, the invention is applied to the movable radiation emitting device 10. However, the invention may be applied to a radiation emitting device that is fixed in an imaging room.

In the above-described exemplary embodiment, in a case in which the radiation detector 80 is included in the captured image G1 and information about, for example, the inclination of the radiation detector 80 is displayed on the monitor 25, the inclination and rotation angle of the monitor 25 are changed. However, the invention is not limited thereto. For example, in a case in which the inclusion of the radiation detector 80 in the captured image G1 is detected, information indicating the detection is transmitted to the radiation emitting device 10, and the detection region 103 is displayed on the monitor 25, the inclination and rotation angle of the monitor 25 may be changed. In addition, in a case in which the control unit 98 of the console 90 detects that the subject H is included in the captured image G1, information indicating the detection is transmitted to the radiation emitting device 10, and the subject H is displayed on the monitor 25, the inclination and rotation angle of the monitor 25 may be changed.

In the above-described exemplary embodiment, the inclination and rotation angle of the monitor 25 may be changed on the basis of the body position of the subject H, that is, on the basis of whether the subject is at an upright position or a decubitus position. Here, in a case in which the subject H is covered with a sheet, the subject is at the decubitus position. An installation stand for installing the radiation detector 80 is included in the captured image G1 of the subject at the upright position. In a case in which an image of the chest of the subject H at the upright position is captured, imaging is performed in a state in which the subject H stands with arms akimbo. Therefore, the control unit 98 of the console 90 recognizes an object in the vicinity of the subject H in the captured image G1 and determines that the subject H is at the decubitus position in a case in which a sheet is included. In contrast, in a case in which the installation stand is included or in a case in which the hands that are on the waist are included, the control unit 98 determines that the subject H is at the upright position. Pressure sensors may be provided at a plurality of positions on the detection surface of the radiation detector 80 and it may be determined whether the subject H is at the decubitus position or the upright position on the basis of the value of pressure detected by the pressure sensors. In this case, the control unit 98 may determine that the subject H is at the decubitus position in a case in which the value of the pressure detected by the plurality of pressure sensors is relatively large and may determine that the subject H is at the upright position in a case in which the value of the pressure is relatively small. Then, the control unit 98 transmits body position information indicating whether the subject H is at the decubitus position or the upright position to the radiation emitting device 10. The radiation emitting device 10 displays the body position information on the monitor 25. In a case in which the subject H is at the decubitus position, the monitor 25 is adjusted to the horizontal state. In a case in which the subject H is at the upright position, the monitor 25 is inclined at a predetermined angle (for example, 90 degrees).

In the above-described exemplary embodiment, it is preferable that the inclination and rotation angle of the monitor 25 are returned to the initial position in a case in which the radiation detector 80 is not included in the captured image G1 or in a case in which the subject is not included in the radiographic image G2 after imaging ends.

In the above-described exemplary embodiment, in a case in which an image of the subject H at the decubitus position is captured, the monitor 25 is in the horizontal state. In this state, in a case in which the vertical direction of the radiation detector 80 included in the captured image G1 is the up-down direction of the captured image G1, the monitor 25 is changed to the rotation angle at which the monitor 25 is vertically long. As such, in a case in which the monitor 25 is at the rotation angle at which the monitor 25 is vertically long, it is preferable that the monitor 25 is inclined in order to easily check the content displayed on the monitor 25. Therefore, in a case in which the monitor 25 is in the horizontal state and the vertical direction of the radiation detector 80 included in the captured image G1 is the up-down direction of the captured image G1, the monitor 25 may be inclined at a predetermined angle.

In a case in which the radiation emitting device 10 according to the above-described exemplary embodiment is used in, for example, an operating room, in some cases, the monitor 25 is put into an antifouling bag in order to prevent the contamination of the radiation emitting device 10. In this case, it is preferable to incline the monitor 25 in order to easily put the monitor 25 into the antifouling bag. Therefore, the following configuration is preferable. The control unit 98 of the console 90 detects the antifouling bag in the captured image G1. In a case in which the antifouling bag is included in the captured image G1, the control unit 98 transmits the detection result to the radiation emitting device 10. The control unit 73 of the radiation emitting device 10 drives the motor 53 of the driving unit 50 to incline the monitor 25 on the basis of the detection result of the antifouling bag.

In some cases, the radiation emitting device 10 according to the above-described exemplary embodiment is used to capture an image of a long region of the subject, such as the entire backbone (entire spine) or the entire leg (entire lower limb). In this case, the radiation detector 80 is disposed so as to be vertically long, is moved along a predetermined movement axis such that movement regions partially overlap each other, and receives radiation transmitted through the same subject H whenever the position changes. A reading operation is performed for the radiation detector 80 whenever radiation is emitted (a radiographic image is recorded) and the radiographic image G2 is acquired by each reading operation. Then, an operation of connecting the radiographic images G2 to combine the radiographic images G2 is performed to a long radiographic image indicating a long part of the subject. As such, in a case in which an image of a long part is captured, the radiation detector 80 is disposed such that the vertical direction thereof is the up-down direction of the captured image G1 and the monitor 25 is inclined. The inclination of the monitor 25 makes it easy to display and observe a long radiographic image.

Figure 23:
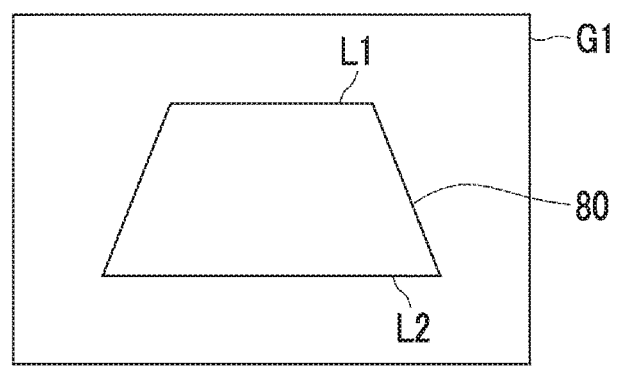
FIG. 23 is a diagram illustrating a captured image including an inclined radiation detector.

In the above-described exemplary embodiment, the inclination of the radiation detector 80 with respect to the horizontal plane is detected on the basis of the inclination information detected by the motion sensor 88 of the radiation detector 80. However, the inclination of the radiation detector 80 with respect to the horizontal plane may be detected on the basis of the image of the radiation detector 80 included in the captured image G1. FIG. 23 is a diagram illustrating a state in which the inclined radiation detector 80 is included in the captured image G1. As illustrated in FIG. 23, in a case in which the inclined radiation detector 80 is included in the captured image G1, there is a difference in length between an upper side L1 and a lower side L2 of the radiation detector 80. Therefore, the control unit 98 of the console 90 calculates the inclination of the radiation detector 80 for matching the upper side L1 with the lower side L2 from the ratio of the upper side L1 to the lower side L2 of the radiation detector 80 included in the captured image G1 and transmits the inclination as the inclination of the radiation detector 80 with respect to the horizontal plane to the radiation emitting device 10. The control unit 73 of the radiation emitting device 10 controls the inclination of the monitor 25 on the basis of the acquired inclination of the radiation detector 80. In a case in which the inclination of the radiation detector 80 is acquired from the radiation detector 80 included in the captured image G1, it is necessary to know the direction of the radiation source unit 40 in advance. Therefore, the control unit 73 of the radiation emitting device 10 acquires the inclination of the radiation detector 80 with respect to the horizontal plane, using the direction of the radiation source unit 40 detected by the angle sensor 49.

In the above-described exemplary embodiment, in addition to the inclination and rotation angle of the monitor 25, the brightness of the monitor 25 is controlled. However, only the inclination and rotation angle may be controlled or only the brightness of the monitor 25 may be controlled. Furthermore, one of the inclination and the rotation angle may be controlled.

In the above-described exemplary embodiment, the inclination and rotation angle of the monitor 25 are controlled on the basis of the display content of the monitor 25. However, the inclination of the monitor 25 may be controlled on the basis of the direction of the radiation source unit 40. In this case, the pivot angle of the radiation source unit 40 detected by the angle sensor 49 is the direction of the radiation source unit 40. Therefore, the control unit 73 may control the inclination of the monitor 25 such that the inclination of the monitor 25 is equal to the pivot angle detected by the angle sensor 49. In this case, it is possible to align the direction of the radiation source unit 40 with the direction of the monitor 25. In addition, in this case, the direction of the radiation source unit 40 may be acquired on the basis of the movement information of the radiation source unit 40 detected by the motion sensor 62 of the radiation source unit 40 and the inclination of the monitor 25 may be controlled on the basis of the acquired direction of the radiation source unit 40.

The inclination and rotation angle of the monitor 25 may be controlled on the basis of the inclination and rotation angle of the radiation detector 80. In this case, the control unit 98 of the console 90 acquires the inclination and rotation angle of the radiation detector 80 about the x-axis on the basis of the movement information detected by the motion sensor 88 of the radiation detector 80 and transmits the information of the calculated inclination and rotation angle to the radiation emitting device 10. The control unit 73 of the radiation emitting device 10 may control the inclination and rotation angle of the monitor 25 on the basis of the received information of the inclination and the rotation angle. In this case, it is possible to match the inclination and rotation angle of the radiation detector 80 with the inclination and rotation angle of the monitor 25. In addition, only the inclination of the monitor 25 may be controlled on the basis of only the inclination of the radiation detector 80 or only the rotation angle of the monitor 25 may be controlled on the basis of only the rotation angle of the radiation detector 80. In a case in which only the rotation angle of the monitor 25 is controlled on the basis of only the rotation angle of the radiation detector 80, the inclination of the monitor 25 may be controlled on the basis of the direction of the radiation source unit 40.

In addition, the inclination of the monitor 25 may be controlled on the basis of both the direction of the radiation source unit 40 and the inclination of the radiation detector. In this case, the control unit 73 may compare the direction of the radiation source unit 40 detected by the angle sensor 49 with the inclination of the radiation detector 80 transmitted from the console 90. In a case in which the direction and the inclination are substantially matched with each other, the inclination of the monitor 25 may be changed. In this case, in a case in which the difference between the direction of the radiation source unit 40 and the inclination of the radiation detector 80 transmitted from the console 90 is, for example, in the range of about ±10 degrees, it may be determined that the direction and the inclination are matched with each other.

A direction change unit 64 that changes the direction of the radiation source unit 40 may be provided in the radiation emitting device 10. The direction change unit 64 includes a driving mechanism, such as a motor for changing the direction of the radiation source unit 40, and a control unit that controls the driving mechanism. The direction change unit 64 corresponds to change unit.

In a case in which the inclination and rotation angle of the monitor 25 are controlled on the basis of the direction and rotation angle of the radiation detector 80, the direction change unit 64 controls the direction of the radiation source unit 40 on the basis of the inclination of the radiation detector 80. In this case, the control unit 73 of the radiation emitting device 10 may instruct the direction change unit 64 to control the direction of the radiation source unit 40 in addition to the inclination and rotation angle of the monitor 25, on the basis of the received information of the inclination and rotation angle of the radiation detector 80. In this case, it is possible to match the inclination and rotation angle of the radiation detector 80, the inclination and rotation angle of the monitor 25, and the direction of the radiation source unit 40. In addition, the control unit 73 of the radiation emitting device 10 may control the direction of the radiation source unit 40 on the basis of the received information of the inclination of the radiation detector 80 and may control the inclination of the monitor 25 on the basis of the controlled inclination of the radiation source unit 40.

Figure 24:
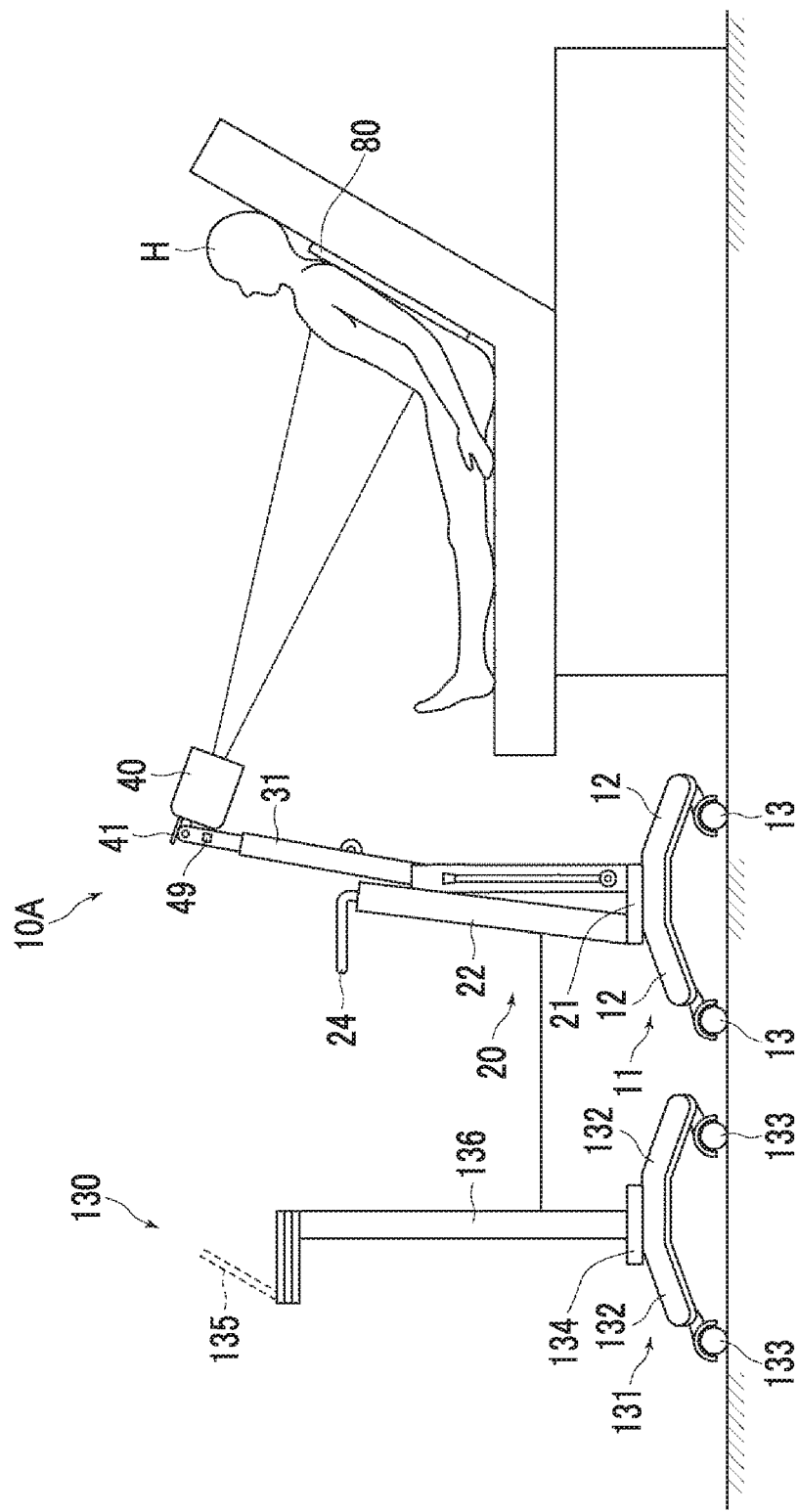
FIG. 24 is a diagram illustrating the usage state of a radiography apparatus including a radiation emitting device in which a monitor is separately provided.

In the above-described exemplary embodiment, the monitor 25 is provided in the radiation emitting device 10. However, the monitor 25 may be separately provided. FIG. 24 is a diagram illustrating a state in a case in which a radiography apparatus including a radiation emitting device in which a monitor is separately provided is used. In FIG. 24, the same components as those in, for example, FIG. 2 and FIG. 16 are denoted by the same reference numerals and the detailed description thereof will not be repeated. In FIG. 24, the console 90 is not illustrated. As illustrated in FIG. 24, the radiography apparatus includes a radiation emitting device 10A that has the same configuration as the radiation emitting device 10 except that it does not include the monitor 25 and a display device 130 including a monitor.

The radiation emitting device 10A has the same configuration as the radiation emitting device 10 except that it does not include the monitor 25. Here, the detailed description thereof will not be repeated. In the display device 130, a base portion 134 is provided on a leg portion 131 including four legs 132 and wheel portions 133 that are attached to the lower surfaces of the leading ends of the legs 132. A support 136 is vertically provided on the base portion 134 and a monitor 135 is attached to the upper end of the support 136.

The monitor 135 includes a driving unit for changing the inclination and rotation angle of the monitor 135, similarly to the above-mentioned monitor 25. The radiation emitting device 10A and the display device 130 perform wired or wireless communication with each other to exchange information.

With this configuration, a control unit of the radiation emitting device 10A transmits a command to change the inclination and rotation angle of the monitor 135 to the display device 130 on the basis of, for example, the display content of the monitor 135. The driving unit (not illustrated) of the monitor 135 changes the inclination and rotation angle of the monitor 135 in response to the command. Therefore, even in a case in which the monitor 135 is provided separately from the radiation emitting device 10A, it is possible to control the inclination and rotation angle of the monitor 135 on the basis of the display content of the monitor 135, as in the above-described exemplary embodiment.

Figure 25:
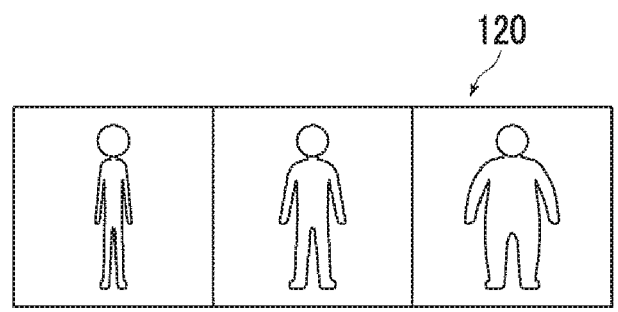
FIG. 25 is a diagram illustrating icons indicating, for example, a thin person, a normal person, and a fat person.

In the above-described exemplary embodiment, the distance sensor 45 detects the SID and the SOD and the body thickness of the subject H is calculated from the SID and the SOD. However, in the radiation emitting device 10, the operator may input the body thickness of the subject H using the input unit 26. In this case, the measured body thickness of the subject H may be input. As illustrated in FIG. 25, icons 120 indicating a thin person, a normal person, and a fat person may be displayed on the monitor 25 such that the operator selects any one of the displayed icons 120 to input the body thickness.

In the above-described exemplary embodiment, the distance sensor 45 measures the SID and the SOD before a pre-imaging operation starts. However, the distance sensor 45 may measure the SID and the SOD during the pre-imaging operation. In this case, a position where the SID and the SOD are measured may be designated on the monitor 25 and the information of the position may be transmitted to the console 90. In this case, it is possible to recognize the position where the body thickness is acquired in the subject H in the console 90.

In the above-described exemplary embodiment, the control unit 98 of the console 90 sets the imaging conditions. However, the control unit 98 may determine whether radiation can be emitted according to the set imaging conditions, on the basis of information about the remaining level of the battery 75 in the radiation emitting device 10. In a case in which radiation is not capable of being emitted according to the set imaging conditions, information indicating that radiation is not capable of being emitted may be transmitted to the radiation emitting device 10. The radiation emitting device 10 may display the information indicating that imaging is not available on the monitor 25 such that the operator can recognize that the remaining level of the battery 75 is insufficient. Therefore, the operator can take, for example, an action of replacing the battery 75 or an action of preparing another radiation emitting device 10.

In the above-described exemplary embodiment, the console 90 may transmit, for example, the captured image G1, the identification information of the radiation detector 80, the radiation detector position information, the information indicating the vertical direction, the center position information, the information indicating the driving state of the radiation detector 80, and the remaining battery level information to a terminal (not illustrated) of a doctor and various kinds of information may be displayed on the terminal so as to be superimposed on the captured image G1, as in the monitor 25. In this case, for example, the doctor can monitor the state of an operation before an image of the subject H is captured in the terminal of the doctor.

In the above-described exemplary embodiment, in some cases, the vertical direction of the radiation detector 80 is the left-right direction of the captured image G1. In some cases, the top and bottom of the radiation detector 80 are opposite to the top and bottom of the captured image G1. In this case, the top and bottom of the acquired radiographic image G2 are not matched with the top and bottom of the captured image G1. Therefore, in a case in which the acquired radiographic image G2 is displayed without any change, it is difficult to see the radiographic image G2. In this exemplary embodiment, the console 90 detects the vertical direction of the radiation detector 80. Therefore, it is possible to rotate the displayed radiographic image G2 such that the top and bottom of the radiographic image G2 are correct. As such, the radiographic image G2 is rotated such that the top and bottom of the radiographic image G2 are correct to match the top and bottom of the radiographic image G2 with the top and bottom of the captured image G1. Therefore, it is possible to easily see the displayed radiographic image G2.

In the above-described exemplary embodiment, in some cases, the amount of movement of the radiation emitting device 10 per unit time is equal to or greater than the threshold value Th1 while radiation is being emitted. In this case, the emission of radiation may be temporarily stopped and radiation may be emitted for the remaining radiation emission time in a case in which the amount of movement of the radiation emitting device 10 per unit time is less than the threshold value Th1. In this case, two radiographic images are acquired before and after the emission of radiation is stopped. The console 90 may combine the two radiographic images using, for example, an addition process to generate a final radiographic image G2.

In the above-described exemplary embodiment, in a case in which preparation for imaging is completed, the radiation field lamp 63 is turned on. However, the turn-on and turn-off of the radiation field lamp 63 may be switched. For example, in a case in which the radiographic image G2 of the face of an animal is acquired, it is necessary to irradiate the face of the animal with radiation. In this case, when the radiation field lamp 63 is turned on, light is emitted to the face of the animal and the animal is likely to become wild. For this reason, the control unit 98 of the console 90 may determine a part of the subject H included in the captured image G1. In a case in which the part is the face of the animal, the control unit 98 may not turn on the radiation field lamp 63 even when preparation for imaging is completed. In this way, it is possible to prevent the animal from becoming wild due to visible light emitted from the radiation field lamp 63. Since the operator knows the part of the subject H, the turn-on and turn-off of the radiation field lamp 63 may be switched by a command input by the operator through the input unit 26.

In the above-described exemplary embodiment, the amount of movement of the radiation emitting device 10 per unit time is calculated using the amount of movement detected by the motion sensor 62. In this exemplary embodiment, the captured image G1 is acquired at a predetermined frame rate. Therefore, the amount of movement of the radiation emitting device 10 per unit time may be calculated on the basis of two captured images acquired at different imaging times and a difference in imaging time between the two captured images.

In the above-described exemplary embodiment, the camera 44 may be an infrared camera that can measure a temperature distribution in an imaging range using infrared rays and an infrared image indicating the temperature distribution in the imaging range may be used as the captured image G1. In this case, the captured image G1 acquired by the camera 44 indicates the temperature distribution of the surface of the subject H and the surface of an object in the vicinity of the subject H. The use of the camera 44 that can acquire an infrared image as the captured image G1 makes it possible to specify the position of the subject H on the captured image G1 on the basis of the temperature distribution indicated by the captured image G1 even in a case in which the subject H is covered with, for example, a sheet in a disaster site.

It is preferable that the camera 44 is switchable between an imaging mode using visible light and an imaging mode using infrared rays. In a case in which the camera 44 that can be switched between the imaging mode using visible light and the imaging mode using infrared rays is used, first, an image of the subject H is captured using infrared rays and the captured image G1 indicating a temperature distribution is acquired. Then, the position of the radiation field is determined using the captured image G1 indicating the temperature distribution. Then, the camera 44 may be switched to the imaging mode using visible light. Then, as in the above-described exemplary embodiment, the detection region of the radiation detector 80 and the radiation field region may be displayed so as to be superimposed on the captured image G1. Then, the position of the radiation detector 80 may be determined using the captured image G1 such that the detection region of the radiation detector 80 and the radiation field region are matched with each other. With this configuration, even in a case in which the subject H is covered with, for example, a sheet, it is possible to match the radiation field region with the detection region of the radiation detector 80 and to acquire the radiographic image G2.

As such, the captured image G1 which is an infrared image is displayed on the monitor 25 such that the operator can recognize abnormality in the body temperature of the subject H. In addition, the captured radiographic image G2 and the captured image G1 which is an infrared image may be displayed side by side on the monitor 25. In this case, the infrared image can be compared with the radiographic image G2.

Next, the operation and effect of the exemplary embodiment of the invention will be described.

The inclination of the radiation detector is matched with the inclination of the display unit. Therefore, it is possible to recognize at which inclination angle the radiographic image is acquired while viewing the display unit.

The direction of the radiation detector is matched with the rotation angle of the display unit. Therefore, it is possible to recognize in which direction the radiographic image is acquired while viewing the display unit.

What is claimed is:

1. A radiation emitting device comprising:
a radiation source for irradiating a subject with radiation;
a camera for capturing an image of the subject to acquire a captured image of the subject;
a monitor for displaying the captured image; and
a computing unit for controlling at least one of an inclination or a rotation angle of the monitor, on a basis of at least one of an inclination of a radiation detector that detects the radiation transmitted through the subject and generates a radiographic image of the subject, a rotation angle of the radiation detector, or a display content of the monitor,
wherein, in a case in which the radiation detector is included in the captured image displayed on the monitor, the computing unit controls at least one of the inclination or the rotation angle of the monitor.

2. The radiation emitting device according to claim 1,
wherein the monitor has a rectangular shape in which a length of two sides opposite to each other in one direction is different from a length of two sides opposite to each other in an other direction,
the radiation emitting device further comprises a driving unit, including at least one motor, for changing at least one of an inclination or a rotation angle of the monitor, and
the computing unit controls the driving unit such that at least one of the inclination or the rotation angle of the monitor is changed, on a basis of at least one of a direction of the radiation source, the inclination of the radiation detector that detects the radiation transmitted through the subject and generates the radiographic image of the subject, or the rotation angle of the radiation detector, or the display content of the monitor.

3. The radiation emitting device according to claim 1,
wherein, in a case in which the inclination of the radiation detector is displayed on the monitor, the computing unit controls at least one of the inclination or the rotation angle of the monitor.

4. The radiation emitting device according to claim 1,
wherein, in a case in which the subject is included in the captured image displayed on the monitor, the computing unit controls at least one of the inclination or the rotation angle of the monitor.

5. The radiation emitting device according to claim 1,
wherein the computing unit controls at least one of the inclination or the rotation angle of the monitor on a basis of a body position of the subject included in the captured image displayed on the monitor.

6. The radiation emitting device according to claim 1,
wherein the computing unit matches the inclination of the monitor with the inclination of the radiation detector.

7. The radiation emitting device according to claim 1,
wherein the computing unit matches the rotation angle of the monitor with the rotation angle of the radiation detector.

8. The radiation emitting device according to claim 1,
wherein the computing unit controls at least one of the inclination or the rotation angle of the monitor on a basis of a display of another image different from the captured image on the monitor.

9. The radiation emitting device according to claim 1,
wherein the computing unit further controls a brightness of the monitor on a basis of a brightness of the captured image.

10. The radiation emitting device according to claim 1,
wherein the captured image is an infrared image, and the monitor displays the infrared image and the radiographic image of the subject.

11. The radiation emitting device according to claim 1, further comprising:
a direction change unit, including at least one motor, for changing a direction of the radiation source, and the direction change unit changes the direction of the radiation source on a basis of the inclination of the radiation detector.

12. The radiation emitting device according to claim 1,
wherein the monitor is provided separately from the radiation source and the camera.

13. The radiation emitting device according to claim 1, further comprising:
a leg portion, including wheels, that is movable on a device mounting surface with the wheels;
a main body portion that is held on the leg portion; and
an arm portion that is connected to the main body portion, wherein the radiation source and the camera are attached to the arm portion,
the monitor is attached to the main body portion, and
the computing unit is accommodated in the main body portion.

14. A method for controlling a radiation emitting device comprising a radiation source for irradiating a subject with radiation, a camera for capturing an image of the subject to acquire a captured image of the subject, and a monitor for displaying the captured image, the method comprising:
controlling at least one of an inclination or a rotation angle of the monitor, on a basis of at least one of an inclination of a radiation detector that detects the radiation transmitted through the subject and generates a radiographic image of the subject, a rotation angle of the radiation detector, or a display content of the monitor,
wherein, in a case in which the radiation detector is included in the captured image displayed on the monitor, the controlling comprises controlling at least one of the inclination or the rotation angle of the monitor.

15. A non-transitory computer-readable recording medium having stored therein a program that causes a computer to perform a method for controlling a radiation emitting device comprising a radiation source for irradiating a subject with radiation, a camera for capturing an image of the subject to acquire a captured image of the subject, and a monitor for displaying the captured image, the method comprising:
controlling at least one of an inclination or a rotation angle of the monitor, on a basis of at least one of an inclination of a radiation detector that detects the radiation transmitted through the subject and generates a radiographic image of the subject, a rotation angle of the radiation detector, or a display content of the monitor,
wherein, in a case in which the radiation detector is included in the captured image displayed on the monitor, the controlling comprises controlling at least one of the inclination or the rotation angle of the monitor.

16. A radiation emitting device comprising:
a radiation source for irradiating a subject with radiation;
a camera for capturing an image of the subject to acquire a captured image of the subject;
a monitor for displaying the captured image; and
a computing unit for controlling at least one of an inclination or a rotation angle of the monitor, on a basis of at least one of a direction of the radiation source, an inclination of a radiation detector that detects the radiation transmitted through the subject and generates a radiographic image of the subject, a rotation angle of the radiation detector, or a display content of the monitor,
wherein, in a case in which the subject is included in the captured image displayed on the monitor, the computing unit controls at least one of the inclination or the rotation angle of the monitor.

17. A method for controlling a radiation emitting device comprising a radiation source for irradiating a subject with radiation, a camera for capturing an image of the subject to acquire a captured image of the subject, and a monitor for displaying the captured image, the method comprising:
controlling at least one of an inclination or a rotation angle of the monitor, on a basis of at least one of a direction of the radiation source, an inclination of a radiation detector that detects the radiation transmitted through the subject and generates a radiographic image of the subject, a rotation angle of the radiation detector, or a display content of the monitor,
wherein, in a case in which the subject is included in the captured image displayed on the monitor, the controlling comprises controlling at least one of the inclination or the rotation angle of the monitor.

18. A non-transitory computer-readable recording medium having stored therein a program that causes a computer to perform a method for controlling a radiation emitting device comprising a radiation source for irradiating a subject with radiation, a camera for capturing an image of the subject to acquire a captured image of the subject, and a monitor for displaying the captured image, the method comprising:
controlling at least one of an inclination or a rotation angle of the monitor, on a basis of at least one of a direction of the radiation source, an inclination of a radiation detector that detects the radiation transmitted through the subject and generates a radiographic image of the subject, a rotation angle of the radiation detector, or a display content of the monitor,
wherein, in a case in which the subject is included in the captured image displayed on the monitor, the controlling comprises controlling at least one of the inclination or the rotation angle of the monitor.

* * * * *